(12) United States Patent
Moltzen et al.

(10) Patent No.: US 6,207,677 B1
(45) Date of Patent: Mar. 27, 2001

(54) PIPERIDINE DERIVATIVES HAVING ANXIOLYTIC EFFECT

(75) Inventors: Ejner K. Moltzen, Frederiksberg C; Jens Kristian Perregaard, Jaegerspris, both of (DK)

(73) Assignee: H. Lundbeck A/S, Copenhagen-Valby (DK)

( * ) Notice: Subject to any disclaimer, the term of this patent is extended or adjusted under 35 U.S.C. 154(b) by 0 days.

(21) Appl. No.: 09/391,290

(22) Filed: Sep. 7, 1999

Related U.S. Application Data

(60) Continuation of application No. 08/486,510, filed on Jun. 7, 1995, now Pat. No. 6,031,099, which is a division of application No. 08/166,647, filed on Dec. 13, 1993, now Pat. No. 5,665,725, which is a continuation of application No. PCT/DK92/00183, filed on Jun. 12, 1992.

(30) Foreign Application Priority Data

Jun. 13, 1991 (DK) .................................................. 1129/91
Jun. 13, 1991 (DK) .................................................. 1131/91
Feb. 10, 1992 (DK) .................................................. 157/92

(51) Int. Cl.$^7$ ........................ A61K 31/438; A61K 31/46; A61K 31/454; A61K 31/4525; A61P 25/00

(52) U.S. Cl. .................... 514/304; 514/278; 514/299; 514/320; 514/321; 514/322; 514/323; 514/324

(58) Field of Search .................................. 514/299, 320, 514/321, 323, 322, 304, 278, 324

(56) References Cited

U.S. PATENT DOCUMENTS

| | | | |
|---|---|---|---|
| 2,891,066 | 6/1959 | Parcell | 260/294.3 |
| 3,135,794 | 6/1964 | Archer | 260/562 |
| 3,408,356 | 10/1968 | Horovitz | 260/294.3 |
| 3,476,760 | 11/1969 | Kaiser et al. | 546/201 |
| 3,558,637 | 1/1971 | Kaiser et al. | 546/201 |

(List continued on next page.)

FOREIGN PATENT DOCUMENTS

| | | |
|---|---|---|
| 247250 | 9/1962 | (AU) . |
| 45869/89 | 6/1990 | (AU) . |
| 2031663 | 6/1991 | (CA) . |
| 16 95 604 | 2/1968 | (DE) . |
| 28 11 031 | 3/1978 | (DE) . |
| 28 27 874 | 6/1978 | (DE) . |
| 0 007 258 A1 | 1/1980 | (EP) . |
| 0 063 799 A3 | 11/1982 | (EP) . |
| 0 112 191 B1 | 6/1984 | (EP) . |
| 0 135 781 A1 | 4/1985 | (EP) . |
| 0 259 782 B1 | 3/1986 | (EP) . |
| 0 200 322 A1 | 11/1986 | (EP) . |
| 0 224 919 A2 | 6/1987 | (EP) . |
| 0 281 309 B1 | 9/1988 | (EP) . |
| 0 302 423 A2 | 2/1989 | (EP) . |

(List continued on next page.)

OTHER PUBLICATIONS

Adachi et al. (1985), "Aminohaloborane in Organic Synthesis. IX. $^{1)}$ Exclusive *Ortho* Acylation Reaction of N–Monoaminoalkylani–lines", *Chem. Pharm. Bull.*, vol.33(5), pp. 1826–1835.

Arnt, J. et al. (1989), "In Vivo Pharmacology of Irindalone, a 5–HT$_2$ Receptor Atanagonist With Predominant Peripheral Effects", *Drug Develop. Res.*, vol. 16, pp. 59–70.

Bally et al. (1887) *Chem. Ber.*, vol. 20, p. 2590.

Barry et al. (1987), "Withdrawal Syndrome Following Subchronic Treatment with Anxiolytic Agents", *Pharmac. Biochem. Behav.*, vol. 27, pp. 239–245.

(List continued on next page.)

*Primary Examiner*—Evelyn Mei Huang
(74) *Attorney, Agent, or Firm*—Darby & Darby

(57) ABSTRACT

Piperidine compounds having the general formula (I),

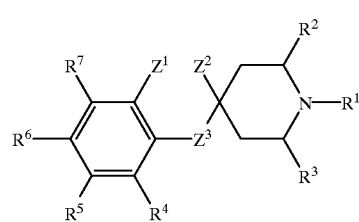

I wherein R$^1$ is (a) a group consisting of alkyl, alkenyl, cycloalkyl, cycloalkenyl, phenyl, cycloalkylalkyl, cycloalkenylalkyl, phenylalkyl or diphenylalkyl linked to the piperidyl N-atom through an at least 2-membered spacer group; or (b) a group having general formula (II),

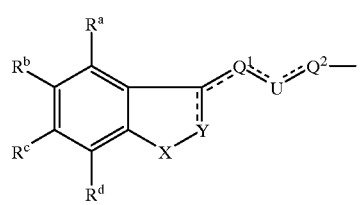

II wherein X is CHR$^{10}$, O, S, SO, SO$_2$ or NR$^{10}$, Z$^1$ is CH$_2$, O, or S; Z$^2$ and Z$^3$ are independently (CH$_2$)$_n$, n being 0 or 1, O or S or Z$^1$ and Z$^2$ may together represent a group —CH=CH—; or when Z$^3$ is (CH$_2$)$_n$ wherein n is 0, Z$^1$ and Z$^2$ may together represent a 3-membered divalent group; show potent sigma receptor activity. Furthermore they show effect in animal models indicative of anxiolytic properties. Accordingly they are useful as medicines for the treatment of anxiety, psychosis, epilepsy, convulsion, movement disorders, motor disturbances, amnesia, cerebrovascular diseases, senile demential of the Alzheimer type or Parkinson's disease.

8 Claims, No Drawings

U.S. PATENT DOCUMENTS

| | | | |
|---|---|---|---|
| 3,686,186 | 8/1972 | Houlihan et al. | 260/293.58 |
| 3,745,165 | 7/1973 | Houlihan et al. | 260/293.58 |
| 3,962,259 | 6/1976 | Bauer et al. | 260/293.58 |
| 3,980,658 | 9/1976 | Possanza et al. | 260/293.61 |
| 3,985,889 | 10/1976 | Bauer et al. | 424/267 |
| 3,993,764 | 11/1976 | Dumont et al. | 424/267 |
| 3,996,211 | 12/1976 | Lassen | 260/240 |
| 4,021,451 | 5/1977 | Dobson | 549/43 |
| 4,038,395 | 7/1977 | Lassen | 424/250 |
| 4,139,634 | 2/1979 | Pigerol et al. | 424/274 |
| 4,166,119 | 8/1979 | Effland et al. | 546/17 |
| 4,196,209 | 4/1980 | Dumont et al. | 424/267 |
| 4,208,417 | 6/1980 | Uzan et al. | 424/267 |
| 4,251,538 * | 2/1981 | Hausberg | 424/267 |
| 4,333,939 | 6/1982 | Guillaume et al. | 424/263 |
| 4,358,456 | 11/1982 | Ward | 424/267 |
| 4,420,485 | 12/1983 | Davis et al. | 424/267 |
| 4,443,448 | 4/1984 | Bøgesø | 424/250 |
| 4,452,802 | 6/1984 | Kosley, Jr. et al. | 424/267 |
| 4,460,594 | 7/1984 | Markwell et al. | 546/201 |
| 4,524,207 | 6/1985 | Ong et al. | 546/17 |
| 4,525,360 | 6/1985 | Perregaard | 514/277 |
| 4,530,932 | 7/1985 | Clemence et al. | 514/318 |
| 4,591,586 * | 5/1986 | Davis | 514/211 |
| 4,670,447 | 6/1987 | Strupczewski | 514/322 |
| 4,684,650 | 8/1987 | Bogeso | 514/252 |
| 4,701,462 | 10/1987 | Wyllie | 514/323 |
| 4,710,500 | 12/1987 | Perregaard | 514/254 |
| 4,772,612 | 9/1988 | Goldmann et al. | 514/302 |
| 4,831,031 | 5/1989 | Lowe, III et al. | 514/254 |
| 4,847,254 | 7/1989 | Boegesoe et al. | 514/256 |
| 4,853,470 | 8/1989 | Strupczewski | 546/199 |
| 4,873,344 | 10/1989 | Bogeso et al. | 541/77 |
| 4,946,863 | 8/1990 | Boegesoe et al. | 514/447 |
| 4,997,841 | 3/1991 | Oxford et al. | 514/323 |
| 5,036,078 | 7/1991 | Coates | 514/323 |
| 5,112,838 | 5/1992 | Perregaard et al. | 514/323 |
| 5,216,001 | 6/1993 | Perregaard et al. | 514/323 |
| 5,219,860 | 6/1993 | Chambers et al. | 514/278 |
| 5,324,733 | 6/1994 | Billington et al. | 514/278 |

FOREIGN PATENT DOCUMENTS

| | | |
|---|---|---|
| 0 376 607 B1 | 7/1990 | (EP). |
| 0 392 959 A2 | 10/1990 | (EP). |
| 0 399 982 A1 | 11/1990 | (EP). |
| 0 414 289 B1 | 2/1991 | (EP). |
| 0 431 943 A2 | 6/1991 | (EP). |
| 0 445 974 A2 | 9/1991 | (EP). |
| 0 465 398 A3 | 1/1992 | (EP). |
| 0 470 039 A2 | 2/1992 | (EP). |
| 1 335 831 | 10/1962 | (FR). |
| 2 391 211 | 4/1976 | (FR). |
| 1 438 094 | 6/1976 | (GB). |
| 55 143980 | 11/1989 | (JP). |
| WO91/09594 | 7/1991 | (WO). |
| WO92/00070 | 1/1992 | (WO). |
| WO92/06089 | 4/1992 | (WO). |
| WO92/10192 | 6/1992 | (WO). |

OTHER PUBLICATIONS

Bøgesø, K. P. et al. (1993), "Stereospecific and Selective 5–HT$_2$ Antagonism in a Series of 5–Substituted trans–1–Piperazino–3–Phenylindans", *J. Med. Chem.*, vol. 36, pp. 2761–2770.

Bøgesø, K. P. et al. (1985), "3–Phenyl–1–indanamines. Potential Antidepressant Activity and Potent Inhibition of Dopamine, Norepinephrine, and Serotonin Uptake", *J. Med. Chem.*, vol. 28, pp. 1817–1828.

Bøgesø, K. P. et al. (1988), "Antihypertensive Activity in a Series of 1–Piperazino–3–phenylindans with Potent 5–HT$_2$ –Antagonostic Activity", *J. Med. Chem.*, vol. 31, pp. 2247–2256.

Bøgesø, K. P. (1983), "Neuroleptic Activity and Dopamine–Uptake Inhibition in 1–Piperazino–3–phenylindans", *J. Med. Chem.*, vol. 26, pp. 935–947.

Casini, G. et al. (1969), "On 1,2–Benzisoxazole–3–acetic Acid and 3–Methyl–1,2–Bennzisoxazole: A Restatement", *J. Het. Chem.*, vol. 6, pp. 279–283.

Gladstone et al. (1965), *J. Chem. Soc.*, vol. 7, 3048.

Greuter et al. (1974), *Helv. Chem. Acta*, vol. 57, p. 281.

Hino, T. et al. (1974), "Bromination of 3–Phenylindoles", *Tetrahedron*, vol. 30, pp. 2123–2133.

Hughes, G. K. et al. (1939), "Researchers of Indoles", *J. Proc. Roy. Soc. N.S. Wales*, vol. 72, pp. 209–221.

Hyttel, J. et al. (1985), "Neurochemical Profile of Lu 19–005, a Potent Inhibitor of Uptake of Dopamine, Noradrenaline, and Serotonin", *J. Neurochem.*, vol. 44, pp. 1615–1622.

Hyttel, J. et al. (1988), "Neurochemical Profile In Vitro of Irindalone: A 5–HT$_2$–Receptor Antagonist", *Drug Dev. Res.*, vol. 15, pp. 389–404.

Iorio, M.A. et al. Farmaco, Ed. Sci. (1997), 32(3):212–219.

Jones, C.D. (1972), *J. Org. Chem.*, vol. 37, p. 3624.

LeFur, G. et al. (1977), "Effects of 4–(3–Indolyl–Alkyl) Piperidine Derivatives on Uptake and Release of Noradrenaline, Dopamine and 5–Hydroxytryptamine in Rat Brain Synaptosomes, Rat Heart and Human Blood Platelets", *Biochem. Pharmacol.*, vol. 26, pp. 497–503.

Martin et al. (1989), "Activity of Aromatic Substituted Phenylpiperazines Lacking Affinity for Dopamine Binding Sites in a Preclinical Test of Antipsychotic Efficacy", *J. Med. Chem.*, vol. 32, pp. 1052–1056.

Mays, R. P. et al. (1980), "Synthesis of 2–Amino–3–Benzoylphenylacetic Acid", *J. Heterocyclic Chem.*, vol. 17, No. 8, pp. 1663–1664.

McElvain, S. M. et al. (1950), "Piperidine Derivatives. XXIII. Certain Halogenated 1–Methyl–4–Phenylpiperidines and Related Compounds", *J. Amer. Chem. Soc.*, vol. 72, pp. 3134–3138.

McMillen, B. A. et al. (1988), "N–Alkyl–Substituted Aryl–Piperazine Drugs: Relationship Between Affinity for Serotonin Receptors and Inhibition of Aggression", *Drug Develop. Res.*, vol. 12, pp. 53–62.

Morooka, S. et al. (1978), "A Convenient Synthesis of 2–Cyano–3–Pheynylindoles", *Synthesis*, No. 6, pp. 445 & 446.

Schulenberg, J. W. et al. (1965), "The Chapman Rearrangement", *Organic Reactions*, vol. 14, pp. 1–51.

Perregaard, J. et al. (1992), "Noncataleptogenic, Centrally Acting Dopamien D–2 and Serotonin 5–HT$_2$ Antagonists within A Series of 3–Substituted 1–(4–Fluorophenyl)–1H–indoles", *J. Med. Chem.*, vol. 35, pp. 1092–1101.

Rao, T. S. et al. (1990), "Inhibition of Climbing and Mossy Fiber, and Basket and Stellate Cell Inputs to Mouse Cerebellar Purkinje Cells by Novel Anti–Ischemic Agents, Ifenprodil and BMY–14802", *Life Sciences*, vol. 47, pp. PL–1–PL–5.

Sanchez et al. (1991), "Neurochemical and In Vivo Pharmacological Profile of Sertindole, a Limbic–Selective Neuroleptic Compound", *Drug Deve. Res.*, vol. 22, pp. 239–250.

Skarsfeldt, T. et al. (1990), "Sertindole, A New Neuroleptic with Extreme Selectivity on A10 Versus A9 Dopamine Neurones in the Rat", *Eur. J. Pharmacol.*, vol. 182, pp. 613–614.

Szabo–Pusztay et al. (1979), "A Simple General Method for the Oxidation of Indoles to Oxindoles", *Synthesis*, vol. 86, pp. 276–277.

C. W. Thornber, Isoterism and Molecular Modification in Drug Design, *Chem. Soc. Rev.*,(1979), 18:563–580.

Ueda et al., "Preparation of Piperidinoalkyl Thiazoles as Antiallergic Agents", Chemical Abstract, vol. 107, Abstract No. 236692F (1987).

Yamamoto, H. et al. (1968), "I–Acylindoles. VII.[1)] On Formation Reaction of Indoles from Phenylhydrazines with Several Acidic Catalysts", *Chem. Pharm. Bull.*, vol. 16, No. 12, pp. 2313–2319.

Rao, Tadimeti S. et al. (1990), "BMY–14802 Antagonizes Harmaline–and D–Serine–Induced Increases in Mouse Cerebellar Cyclic GMP: Neuorochemical Evidence for a σ Receptor–Mediated Functional Modulation of Responses Mediated by the N–Methyl–D–aspartate Receptor Complex In Vivo", *Molecular Pharmacology*, vol. 37, pp. 978–982.

Allen, R. C. et al. (1978), "Synthesis of Spiro [isobenzofuran–1(3H), 4'–piperidines] as Potential Central Nervous System Agents. 4. Central Nervous System Depressants", *J. Med. Chem.*, vol. 21, No. 11, pp. 1149–1154.

Chambers, M. S. et al. (1992), "Spiropiperidines as High–Affinity, Selective α Ligands", *J. Med. Chem.*, vol. 35, pp. 2033–2039.

Marxer et al. (1975), "Spiro Piperidines. I. Synthesis of Spiro[isobenzofuran–1(3H), 4'–Piperidines] and Spiro [isobenzofuran–1(3H,3'–piperidines]", *J. Org. Chem.*, vol. 40, No. 10, pp. 1427–1433.

Yamato, M. et al. (1981)," Synthesis and Structure–Activity Relationship of Spiro[isochromanpiperidine] Analogs for Inhibition of Histamine Release", *Chem. Pharm. Bull.*, vol. 29, No. 12, pp. 3494–3498.

Yamato, M. et al. (1981), "Synthesis and Structure–Activity Relationship of Spiro[isochromanpiperidine] Analogues for Inhibition of Histamine Release", *J. Med. Chem.*, vol. 24, pp. 194–198.

Martin, PT et al. (1994), "Efficacy and Safety of Sertindole in Two Double–Blind, Placebo–Controlled Trials of Schizophrenic Patients", *Schizophrenia Research*, vol. 11, p. 107.

Snyder, S.H. et al. (1989), "Receptor Mechanisms in Antipsychotic Drug Action: Focus on Sigma Receptors," *Neuropsychiatry*, vol. 1, p. 7.

Colpaert et al. (1987) *Br. J. Pharmacology*, vol. 90, p. 275.

* cited by examiner

PIPERIDINE DERIVATIVES HAVING ANXIOLYTIC EFFECT

This is a continuation application of U.S. patent application Ser. No. 08/486,510 filed Jun. 7, 1995, U.S. Pat. No. 6,031,099 which is divisional application of U.S. patent application Ser. No. 08/166,647 filed Dec. 13, 1993, U.S. Pat. No. 5,665,725 which is a continuation of International application no. PCT/DK92/00183 filed Jun. 12, 1992.

The present invention relates to a class of piperidine compounds having anxiolytic effect, and potently binding to the sigma receptors and therefore being useful in the treatment of psychic and neurologic disorders.

Various related compounds are known from the prior art.

So, U.S. Pat. Nos. 3,686,186 and 3,745,165 disclose spiro[phthalan-1,4'-piperidine] and spiro[isochroman-3,4'-piperidine] compounds optionally having a benzyl substituent at the piperidine N-atom. The phthalan compounds are said to be useful as antidepressants as indicated by their ability to reverse reserpine hypothermia, whereas the isochromane compounds are stated to be useful as hypotriglyceridemics.

German Offenlegungsschrift No. 2,458,176 and the corresponding U.S. Pat. No. 3,985,889 generically describe inter alia 1,3-dihydrospiro[isobenzofuran-1,4-piperidine] or 1,3-dihydrospiro[isobenzofuran-1,3'-pyrrolidine] compounds substituted at the ring N-atom with lower alkyl, cycloalkyl or phenyl($C_{2-4}$)alkyl and optionally having an oxo group attached to the furan ring. The compounds are alleged to be useful as tranquilizers as demonstrated by their ability to display effects on behaviour and reflex depression and on muscle relaxation, and they are claimed also to be useful in the treatment of pain as demonstrated in the 2-phenyl-1,4-quinone induced writhing assay in mice. However, only pharmacological data for one such compound without an oxo substituent in the furan ring, i.e. the compound 1,3-dihydro-1'-methyl-spiro[isobenzofuran-1,4'-piperidine], are presented, and only four such compounds having a substituent different from methyl on the piperidine N-atom are specifically disclosed, i.e. 1'-cyclopropylmethyl-, 1'-[3-(4-fluoro-benzoyl)propyl]-, 1'-[4,4-bis(4-fluorophenyl)butyl]- and 1'-acetyl-1,3-dihydrospiro[iso-benzofuran-1,4'-piperidine]. No indication of effect on sigma-receptors is given.

Japanese patent publication JP Kokai 55 143,980 generically describes inter alia a very broad class of spiro [chromane-piperidine] compounds which are optionally substituted at the piperidine N-atom with an alkyl, cycloalkyl, allyl, aryl, aralkyl, or arylcycloalkyl group and optionally substituted in the chromane ring with an oxo group. However, with respect to such spirochromane compounds having no oxo substituent in the chromane ring only compounds having a methyl, phenyl or benzyl group at the piperidine N-atom are specifically disclosed. These compounds are claimed to possess antiallergic activity and no suggestion of activity in the central nervous system is given.

European patent publication No EP 0 414 289 A1 generically describes a class of 1,2,3,4-tetrahydro-spiro [naphthalene-1,4'-piperidine] and 1,4-dihydro-spiro [naphthalene-1,4'-piperidine] derivatives substituted at the piperidine N-atom with a "hydrocarbon" and aleged to have selective sigma receptor antagonistic activity. The term "hydrocarbon" as defined in said patent covers all possible straight chained, cyclic, heterocyclic etc. groups; however, only compounds having benzyl, phenethyl, cycloalkylmethyl, furyl- or thienylmethyl or lower alkyl or alkenyl as the "hydrocarbon". substituent at the piperidine nitrogen atom being specifically disclosed. The compounds are stated to displace tritiated di-tolyl guanidine (DTG) from sigma sites with potencies better than 200 nM. As a particularly preferred compound is mentioned 1'-benzyl-1,2,3,4-tetrahydro-spiro[naphthalene-1,4'-piperidine]. European patent publication No EP 0 445 974 A2 generically describes the corresponding spiro[indane-1,4'-piperidine) and spiro [benzocycloheptene-5,4'-piperidine] derivatives. Again the compounds are only stated to displace tritiated ditolyl guanidine (DTG) from sigma sites with potencies better than 200 nM EP Application No. EP-A2-0 431 943 relates to a further extremely broad class of spiropiperidine compounds substituted at the piperidine N-atom. Said compounds are alleged to be useful as antiarrythmics and for impaired cardiac pump function.

Said application exemplifies several compounds, the majority of which contain an oxo and/or a sulfonylamino substituent in the spiro cyclic ring system. Of the remainder compounds, the main part has another polar substituent, such as nitro, amino, a fused imidazo group etc. attached to the spiro nucleus and/or they have some polar substituents, such as sulfonylamino, nitro, amino, etc. in the substituent on the piperidine N-atom. Furthermore some of the compounds have heteroaryl alkyl substituents on the piperidine N-atom, whereas only a very few of those compounds exemplified do not have such substituents, i.e. a couple of 6-methoxy-spiro[2H-1-benzopyran-2,4'-piperidines] having a phenylsubstituent on the piperidine N-atom and a few spiro[3H-1-benzopyran-3,4'-piperidine]'s having a benzyl, phenethyl, hexyl or heptyl substituent on the piperidine N-atom. No suggestion or indication of effect of the compounds on the sigma receptors is given.

U.S. Pat. No. 4,420,485 discloses 1'-[3-(6-fluoro-1,2-benzoisoxazol-3-yl)propyl]spiro[benzofuran-2(H),4'-piperidines3 optionally having one or two substituents in the benzofuran ring. The compounds are claimed to be useful as antihypertensives. No mention or suggestion of effects in the treatment of psychic or neurological disorders is given.

German Offenlegungsschrift No 28 27 874 corresponding to U.S. Pat. No. 4,251,538 generically discloses a class of 3-[4-(4-phenyl-piperidin-1-yl)-butyl]- or 3-(4-(4-phenyl-tetrahydropyridyl-1-yl)-butyl]indole derivatives optionally substituted in the indole, piperidinyl or tetrahydropyridyl and/or phenyl groups. The compounds are said to show dopamine agonist effects and serotonin reuptake inhibiting effects in the central nervous system, and accordingly to be useful in the treatment of Parkinson's disease and depression. However, no documentation for such effects is given in the specification, no pharmacological data at all being given, and certainly no indication or suggestion of effect on the sigma receptor is given.

Furthermore, the majority of the compounds listed in the specification, of which obviously only a few have actually been prepared, are tetrahydropyridyl compounds and/or they have an oxo substituent in the butyl chain. Only a few piperidyl compounds without an oxo substituent in the butyl chain are mentioned, i.e. 3-[4-(4-phenyl-1-piperidyl)-butyl]-indole and the 1-methyl-, 1-phenyl- and 2-methyl-derivatives thereof as well as derivatives thereof substituted with halogen, methyl or trifluoromethyl in the 4-phenyl substituent on the piperidyl group thereof. With respect to physical data only melting point for one such compounds is given.

International Patent Application No WO 91/09594 published on Jul. 11, 1991 relates i.a. to sigma receptor ligands being 4-phenyl-piperidine compounds and having an optionally substituted "heteroaryl"-alkyl, -alkenyl, -alkynyl, -alkoxy or -alkoxy-alkyl substituent on the piperidine N-atom. The term "heteroaryl"-alkyl is defined by mention of a very broad class of such substituents. However only four N-substituted 4-phenyl-piperidine compounds are specifically disclosed which are all 1-(phenyl-lower alkyl)-4-phenyl-piperidines and only four compounds having a "heteroaryl"-alkyl substituent are specifically mentioned, which are all piperazine (and not piperidine) compounds. The compounds are stated to be antipsychotics.

From studies of the biology and function of sigma receptors, evidence has been presented that sigma receptor ligands may be useful in the treatment of psychosis and movement disorders, such as dystonia and tardive dyskinesia, and motor disturbances associated with Huntington's chorea or Tourette's syndrome and in Parkinson's disease (Walker, J. M. et al., *Pharmacological Reviews*, 1990, 42, 355). The known sigma receptor ligand rimcazole clinically shows effects in the treatment of psychosis (Snyder, S. H., Largent, B. L. *J. Neuropsychiatry* 1989, 1, 7) and a group of sigma receptor ligands have been described to show antihallucinogenic activity in animal models (International Patent Publication No WO 9/03243).

Furthermore, sigma receptor ligands have been reported to be involved in modulation of NMDA receptor mediated events in the brain and to act as anti-ischemic agents in in vivo tests (Rao, T. S. et al, *Molecular Pharmacology*, 1990, 37, 978). In addition to ischemia they may also be useful in the treatment of other such NMDA receptor mediated events, e.g. epilepsy and convulsion.

Also, some sigma receptor ligands have been found to show anti-amnesic effects in an animal model (Early et al., *Brain Research* 1991, 546, 281–286). Sigma ligands have been shown to influence central acetylcholine levels in animal models (Matsuno et al, Brain Research 1992, 575, 315–319; Junien et al, Eur. J. Pharm. 1991, 200, 343–345) and may, therefore, have potential in the treatment of senile dementia of the Alzheimer type.

Finally, some guanidine derivatives having sigma receptor activity have been disclosed to be useful as anxiolytics (International Patent Publication No. WO 9014067).

Accordingly, agents potently acting on the sigma receptors in the central nervous system are believed to be of potential use in the therapy of such conditions.

It has now been found that a certain class of piperidine compounds bind at sigma receptors with potencies which generally are 2–3 orders of magnitude higher than the potency limit indicated in European patent publication EP 0 414 289 A1. Furthermore the compounds of said class have been found to show anxiolytic effects in animal models.

Said class of compounds consists of compounds having the general Formula I

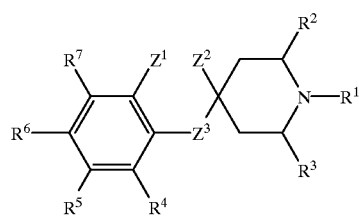

I wherein $R^1$ is a) a group -D-B-A-R wherein B is an up to 19 membered spacer group selected from alkylene, alkenylene and alkynylene which may be branched or straight chain and optionally substituted with hydroxy, which again may be esterified with an aliphatic carboxylic acid having from two to twentyfour carbon atoms, inclusive, A is a bond or a divalent group selected from O, S, SO, $SO_2$, and

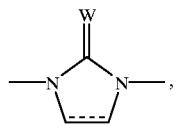

W being O or S and the dotted line designating an optional bond;

R is alkyl, alkenyl, cycloalkyl, cycloalkenyl, phenyl, cycloalkylalkyl, cycloalkenylalkyl, phenylalkyl, diphenylalkyl, any alkylgroup optionally being substituted with one or two hydroxy groups, which again may be optionally esterified with an aliphatic carboxylic acid having from two to twentyfour carbon atoms inclusive, and any phenyl group being optionally substituted with one or more substituents in the phenyl ring; and D is $CR^8R^9$ where $R^8$ and $R^9$ are independently selected from the substituents defined below for $R^4$–$R^7$, or a cycloalkylene group; or b) a group having the general Formula II:

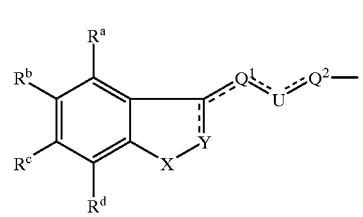

II wherein X is $CHR^{10}$, O, S, SO, $SO_2$ or $NR^{10}$, $R^{10}$ being hydrogen, lower alkyl or alkenyl, cycloalkyl or cycloalkylalkyl, cycloalkenyl, or cycloalkenylalkyl, acyl, aminoalkyl, mono- or dialkylaminoalkyl, sulfonyl or aryalkyl or phenyl optionally is substituted with one or more substituents independently selected from the following: halogen, lower alkyl, lower alkoxy, hydroxy, trifluoromethyl, and cyano, or $R^{10}$ is a hetero aromatic group, preferably 2-thienyl, 3-thienyl, 2-furanyl, 3-furanyl, 2-thiazolyl, 2-oxazolyl, 2-imidazolyl, 2-pyridyl, 3-pyridyl, or 4-pyridyl;

one or two of the dotted lines may be a bond;

when the dotted line emanating from Y indicates a bond, Y is N or CH; or when said dotted line indicates no bond, Y is $CH_2$, NH, C=O or C=S;

$R^a$–$R^d$ are independently selected from hydrogen, halogen, lower alkyl, lower alkoxy, hydroxy, lower alkylthio, lower alkylsulphonyl, lower alkyl- or dialkylamino, cyano, trifluoromethyl, or trifluoromethylthio;

U is $CH_2$, O or S; or when, one of the dotted lines emanating from U indicates a bond, U is CH;

the bond between U and $Q^1$ or $Q^2$, respectively, may also be a triple bond and in such case U is "C";

$Q^1$ is selected from a bond, alkylene or alkenylene and $Q^2$ is alkylene having at least two C-atoms, alkenylene or a group $Q^{2'}D$ wherein $Q^{2'}$ is as defined for $Q^2$ and D is as defined above, $Q^1$ and $Q^2$ having together from 2 to 20 carbon atoms and being optionally substituted with one or more hydroxy groups, any such hydroxy group being optionally esterified with an aliphatic carboxylic acid having from two to twentyfour carbon atoms inclusive; and $R^2$ and $R^3$ are independently hydrogen, lower alkyl or they may be linked together thereby forming an ethylene or propylene bridge;

$R^4$ to $R^7$ are independently selected from hydrogen, halogen, lower alkyl lower alkoxy, hydroxy, lower alkylthio, lower alkyl- or dialkylamino, cyano, trifluoromethyl, or trifluoromethylthio; and i) $Z^1$ and $Z^2$ are linked together in which case: $Z^1$ is $CH_2$, O or S; $Z^2$ and $Z^3$ are independently $(CH_2)_n$, n being 0 or 1, O or S, with the proviso that $Z^1$ may not be S or O when $Z^2$ is S or O, and that $Z^2$ and $Z^3$ may not both be $(CH_2)_n$ wherein n is 0: or $Z^1$ and $Z^2$ may together represent a group —CH=CH—; or when $Z^3$ is $(CH_2)_n$ wherein n is 0, $Z^1$ and $Z^2$ may together represent a 3-membered divalent group, optionally containing one unsaturated bond, and optionally containing one O- or S-heteroatom; or ii) when $R^1$ is a group as defined in b) $Z^1$ and $Z^2$ may also be unlinked, in which case: $Z^1$ is a group as defined for $R^4$–$R^7$, $Z^2$ is hydrogen and $Z^3$ is $(CH_2)_n$ wherein n is 0; with the proviso that when $Z^1$–$Z^3$ are as defined in i) wherein $Z^3$ is $(CH_2)_n$ where n is 0, and $Z^1$ and $Z^2$ together represent a 2- or 3-membered divalent hydrocarbon group, optionally containing one unsaturated bond, and $R^1$ is a group defined in a) then D-B-A-R may not be phenyl-$C_{1-3}$-alkyl, lower alkyl or lower alkenyl; and acid addition salts or prodrugs thereof.

Accordingly the present invention provides the use of piperidine compounds having the above defined general Formula I or acid addition salts or prodrugs thereof for the manufacture of a pharmaceutical preparation for the treatment of anxiety, psychosis, epilepsy, convulsion, movement disorders, motor disturbances, amnesia, cerebrovascular diseases, senile dementia of the Alzheimer type or Parkinson's disease.

Some of the compounds of the general Formula I may exist as optical-isomers thereof; and such optical isomers are also embraced by the invention.

The term alkyl is intended to mean a $C_1$–$C_{20}$ straight chain or branched alkyl group and similarly alkenyl means a $C_2$–$C_{20}$ straight chain or branched alkenyl group having one or more unsaturated bonds in the chain. The term cycloalkyl designates a carbocyclic ring having 3–8 carbon atoms inclusive or a bicyclic or tricyclic carbocycle, such as adamantyl.

The terms lower alkyl, lower alkoxy, lower alkylthio, etc. designate such branched or is unbranched groups having from one to six carbon atoms inclusive. Exemplary of such groups are methyl, ethyl, 1-propyl, 2-propyl, 1-butyl, 2-butyl, 2-methyl-2-propyl, 2-methyl-1-propyl, methoxy, ethoxy,1-propoxy, 2-propoxy, methylthio, ethylthio, 1-propylthio, 2-propylthio, methylsulphonyl, ethylsulphonyl, or the like.

Halogen means fluoro, chloro, bromo or iodo.

The term "sulfonyl" is used in the meaning alkyl or aryl substituted sulfonyl, and similarly "acyl" is used in the meaning alkyl- or arylcarbonyl The term "one or two of the dotted lines may be a bond" is intended to mean that each of the dotted lines may or may not represent a bond, i.e. that the ring and the side chain respectively may or may not have a double bond in the positions of the dotted lines in Formula II, provided that only two at a time indicate a bond and that adjacent dotted lines do not both indicate a bond.

The optional substituents in the phenyl groups in the definition af R may independently be selected from halogen, lower alkyl, lower alkoxy, hydroxy, lower alkylthio, lower alkylsulphonyl, lower alkyl- or dialkylamino, cyano, trifluoromethyl, or trifluoromethylthio. Each phenyl group may carry one or more substituents.

The acid addition salts of the invention are pharmaceutically acceptable salts of the compounds of Formula I formed with non-toxic acids. Exemplary of such organic salts are those with maleic, fumaric, benzoic, ascorbic, embonic, succinic, oxalic, bis-methylenesalicylic, methanesulfonic, ethanedisulfonic, acetic, propionic; tartaric, salicylic, citric, gluconic, lactic, malic, mandelic, cinnamic, citraconic, aspartic, stearic, palmitic, itaconic, glycolic, p-aminobenzoic, glutamic, benzene sulfonic and theophylline acetic acids, as well as the 8-halotheophyllines, for example 8-bromotheophylline. Exemplary of such inorganic salts are those with hydrochloric, hydrobromic, sulfuric, sulfamic, phosphoric and nitric acids.

The movement disorders and motor disturbances which may be treated by the preparation according to the invention are e.g. dystonia and tardive dyskinesia and is motor disturbances associated with Huntington's chorea or Tourette's syndrome. Dystonia may be acute or tardive and may be caused by neuroleptics or have another reason.

Cerebrovascular diseases are such disorders caused by cerebral infarction, cerebral hemorrhage, cerebral arteriosclerosis, subarachnoid hemorrhage, cerebral thrombosis, cerebral embolism, or the like, e.g. ischemia, hypoxia, anoxia.

The compounds of the invention have been found to displace tritiated di-tolyl guanidine (DTG) from sigma sites in vitro with potencies better than about 40 nM, and the great majority better than 1 nM, i.e. they are binding at the sigma receptors much more potently than sigma receptor ligands such as e.g. BMY 14802 and rimcazole. Furthermore, most of the present compounds have proven to be very selective ligands on the sigma receptors. For example as compared to the a, adrenoceptors and dopamine $D_2$ receptors, the main part of the present compounds have been found to show ratios of binding affinities ($IC_{50}$ alpha/sigma and dopamine/sigma, respectively) of 30–10000. Furthermore, the compounds have proven to show very potent anxiolytic effects in an animal behaviour test in extremely low doses i.e. with $EC_{50}$ values in the ng–$\mu$g/kg range.

When $Z^1$ and $Z^2$ are linked together, preferably at least one of $Z^1$, $Z^2$ and $Z^3$ designates O or S, and more preferably $Z^3$ is $(CH_2)_n$ wherein n is 0, and Z2 is "O" or "S" and Z) is $CH_2$ or $Z^1$ and $Z^2$ together represent $CH_2$—O—$CH_2$. Other preferred groups are those wherein $Z^1$ is $CH_2$, $Z^2$ is O and $Z^3$ is $CH_2$; or $Z^3$ is O and $Z^1$–$Z^2$ is CH=CH; or $Z^1$ is O, $Z^3$ is O and $Z^2$ is $(CH_2)_n$ where n=0, Particularly preffered compounds are:

1'-(3-Adamantyloxy-1-propyl)spiro[3 H-2-benzopyran-3,4'-piperidine];

1'-[4-(1-Benzyl-3-indolyl)-1-butyl]-spiro[isobenzofuran-1(3H),4'-piperidine];

1'-(3-(3-Phenylimidazolidin-2-on-1-yl)-1-propyl)spiro[isobenzofuran-1(3H),4'-piperidine];

1'-[4-[1-(4-Fluorophenyl)-3-indolyl]1-butyl]-spiro[isobenzofuran-1(3H),4'-piperidine];

1,4-Dihydro-1'-[4-[1-(4-Fluorophenyl)-3-indolyl]-1-butyl]spiro[3H-2-benzopyran-3,4'-piperidine];

1'-(4-(1-p-Toluenesulfonyl-3-indolyl)-1-butyl)spiro[isobenzofuran-1(3H),4'-piperidine];

1'-[4-[5-Fluoro-1-(4-fluorophenyl)-3-indolyl]-1-butyl]spiro[isobenzofuran-1(3H), 4'-piperidine];

6-Fluoro-1'-[4-[1-(4-fluorophenyl)-3-indolyl]-1-butyl]spiro[isobenzofuran-1(3H),4'-piperidine];

1'-[4-[1-(4-Methylphenyl)-3-indolyl]-1-butyl]spiro[1H-2-benzopyran-4(3H),4'-piperidine];

1-(4-Fluorophenyl)-3-[4-(4-(4-fluorophenyl)-1 -piperidyl)-1-butyl]indole;

1'-[4-(1-(2-Thiazolyl)-3-indolyl)-1-butyl]spiro[isobenzofuran-1(3H),4'-piperidine];

1'-[3-(5-Fluorobenzofuran-3-yl)-1-propyl]spiro[isobenzofuran-1(3H),4'-piperidine];

1'-[4-(5-Fluorobenzofuran-3-yl)-1-butyl]-spiro[isobenzofuran-1(3H),4'-piperidine]

1'-[4-[1-(4-Fluorophenyl)-5-trifluoromethylindazol-3-yl]-1-butyl]spiro[isobenzofuran-1(3H),4'-piperidine];

4-Fluorophenyl-3-[4-(4-(4-fluorophenyl)-1-piperidinyl)-1-butyl]-5-trifluoro methylindazol;

1'-(4-(1,2-Benzisoxazol-3-yl)-1-butyl)spiro[isobenzofuran-1(3H),4'-piperidine]; and 1'-[3-(Benzo[b]thiophen-3-ylthio)-1-propyl]spiro[isobenzofuran-1(3H),4'-piperidine].

Some of the compounds used in accordance with the invention are novel, and accordingly in another aspect the present invention relates to novel piperidine derivatives having the general Formula I as defined above with the proviso that if $R^1$ is a group of the Formula II as defined above under b), $Z^1$, $Z^2$, and $Z^3$ are as defined above under ii), X is NH, Y is CH and the dotted line emanating from Y indicates a bond, then —$Q^1$—U—$Q^2$— may not be alkyl having less than 5 carbon atoms;

if $R^1$ is a group of the Formula II as defined above wherein $Z^3$ is O, $Z^1$ is $CH_2$, $Z^2$ is $(CH_2)_n$, n being O, X is O, Y is N, the dotted line emanating from Y indicates a bond, and —$Q^1$—U-$Q^2$— indicates —$(CH_2)_3$, then $R^c$ may not be fluoro;

if $Z^3$ is O, $Z^2$ and $Z^1$ are both $CH_2$ and D-B-A-R is optionally substituted phenethyl, then $R^6$ may not be methoxy; and if $Z^1$ is O, and $Z^2$ and $Z^3$ are both $CH_2$, then D-B-A-R may not be phenethyl, or optionally hydroxy substituted hexyl or heptyl.

The present invention also provides a pharmaceutical composition comprising at least one novel piperidine compound according to the invention as defined above or a pharmaceutically acceptable acid addition salt thereof or prodrug therefore in combination with one or more pharmaceutically acceptable carriers or diluents.

The pharmaceutical compositions of this invention or those which are manufactured in accordance with this invention may be administered by any suitable route, for example orally in the form of tablets, capsules, powders, syrups, etc., or parenterally in the form of solutions for injection. For preparing such compositions methods well known in the art may be used, and any pharmaceutically acceptable carriers, diluents, exipients, or other additive usually used in in the art may be used.

Conveniently, the compounds of the invention are administered in unit dosage form containing said compound in an amount of about 0.01 to 50 mg.

The total daily dose usually ranges of about 0.05–100 mg, and most preferably about 0.1 to 20 mg of the active compound of the invention.

The compounds of Formula I may be prepared by:

a) reducing the amide carbonyl of a compound of Formula III

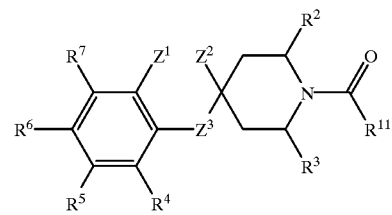

III wherein $R^2$–$R^7$ and $Z^1$–$Z^3$ are as previously defined and $R^{11}$ is such a group that $CH_2$—$R^{11}$ is a group comprised by the definition of $R^1$;

b) alkylating a compound of Formula IV

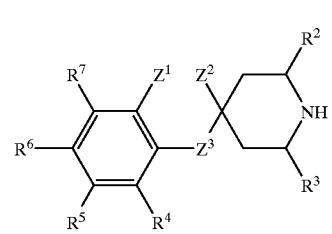

IV wherein $R^2$–$R^7$ and $Z^1$–$Z^3$ are as previously defined, with an alkylating reagent of the formula $R^1$-V wherein $R^1$ is as previously defined and V is a suitable leaving group such as halogen, mesylate ortosylate;

c) reductive alkylation of amines of Formula IV with aldehydes of the formula $R^{11}$-CHO or carboxylic acids of the formula $R^{11}$-COOH or ketones of the formula $R^{12}$-CO-$R^{13}$ wherein $R^2$–$R^7$, $R^{11}$, and $Z^1$–$Z^3$ are as previously defined and $R^{12}$ and $R^{13}$ are such groups that $R^{12}$-CH-$R^{13}$ is a group comprised by the definition of $R^1$;

d) reducing the C=$Y^1$ double bond in a compound of Formula V

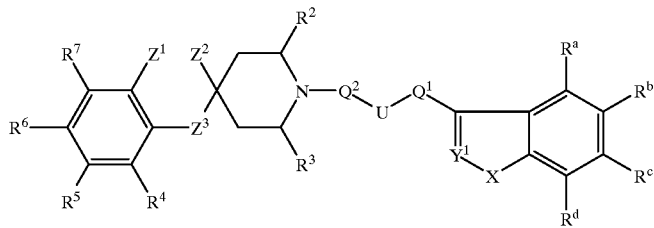

V wherein $R^a$–$R^d$, X, U, $Q^1$, $Q^2$, $R^2$–$R^7$, and $Z^1$–$Z^3$ are as previously defined and $Y^1$ is CH or N;

e) oxidizing a compound of Formula VI to an oxo compound of Formula VII:

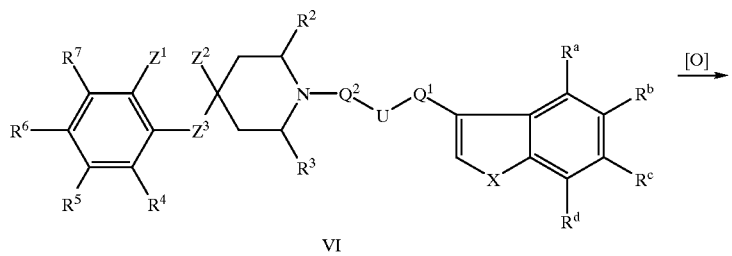

VI

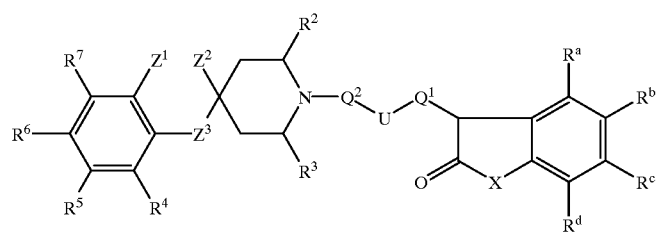

VII wherein $R^a$–$R^d$, X, U, $Q^1$, $Q^2$, $R^2$–$R^7$, and $Z^1$–$Z^3$ are as previously defined;

f) alkylating a compound of Formula VIII for obtaining a compound of general Formula I wherein X=NR$^{10'}$, R$^{10'}$ being lower alkyl, alkenyl, cycloalkyl, cycloalkylalkyl, cycloalkenyl or cycloalkenylalkyl, the group R$^{10'}$, and subsequently reducing the acylated compound of Formula VII;

g) arylating a compound of Formula VII for obtaining a compound of general Formula I wherein X=NR$^{10'''}$, R$^{10'''}$ being optionally substituted phenyl or heteroaryl, with an arylating agent of the formula Ar-V$^1$ wherein Ar is optionally substituted phenyl or heteroaryl and VI is as previously defined, h) for obtaining a compound of general Formula I wherein X=N-CO-R$^{10'}$ or N-CO-Ar, wherein R$^{10'}$ and Ar are as

VIII

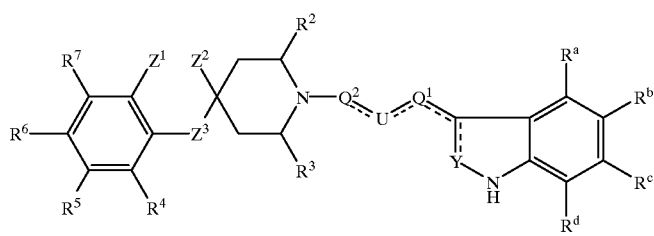

wherein $R^a$–$R^d$, Y, U, $Q^1$, $Q^2$, $R^2$–$R^7$, and $Z^1$–$Z^3$ are as previously defined, with an alkylating reagent of the formula R$^{10}$-V$^1$, wherein R$^{10'}$ is as previously defined and V$^1$ is a suitable leaving group, e.g. halogen, mesylate, or tosylate; or acylating a compound of the Formula VIII with an acylating reagent having the formula R$^{10''}$-CO-Hal, wherein Hal is halogen and R$^{10''}$ is a group which together with CH$_2$ form previously defined, acylating a compound of Formula VIII with an acylating agent of the formula R$^{10'}$-CO-Hal or Ar-CO-Hal, wherein Hal is as previously defined;

i) for obtaining a compound of general Formula I wherein X=N-SO$_2$-R$^{10'}$or N-SO$_2$-Ar, wherein R$^{10'}$ and Ar are as previously defined, sulfonylating a compound of Formula VIII with a sulfonylating agent of the formula $R^{10'}-SO_2-Hal$ or $Ar-SO_2-Hal$, wherein Hal is as previously defined;

j) reductive alkylation of compounds of Formula VIII with carbonyl compounds of formula $R^{14}CO-R^{15}$ wherein $R^{14}$ and $R^{15}$ are such groups that $R^{14}-CH-R^{15}$ is a group $R^{10}$ as previously defined;

k) making a ring closure reaction of the hydrazone IX to the indazole derivative X

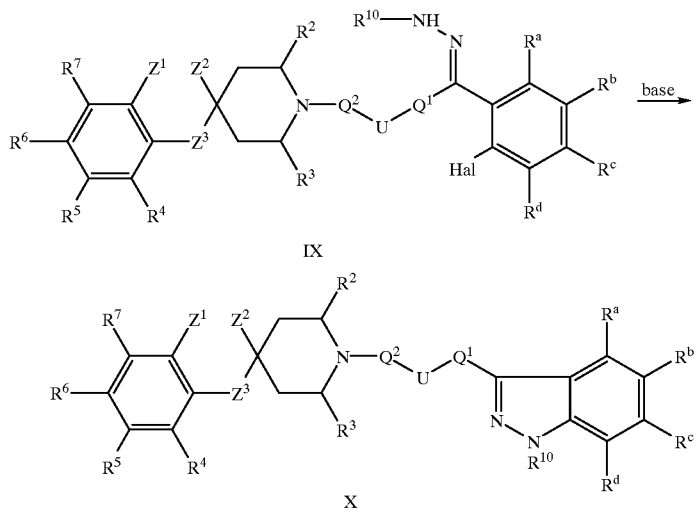

wherein $R^a$–$R^d$, U, $Q^1$, $Q^2$, $R^2$–$R^7$, $R^{10}$, and $Z^1$–$Z^3$ are as previously defined and Hal is halogen;

l) reducing the quarternized pyridine derivative of Formula XI

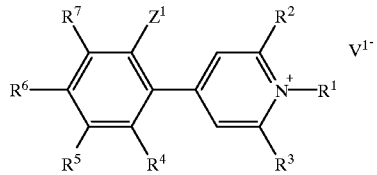

in which $R^1$–$R^7$, $Z^1$ and $V^1$ are as previously defined; whereupon the compound of Formula I is isolated as the free base or a pharmaceutically acceptable acid addition salt thereof.

The reduction according to method a) may preferably be carried out in an inert organic solvent such as diethyl ether or tetrahydrofuran in the presence of lithium aluminium hydride at reflux temperature.

The amides of Formula III are conveniently prepared by treating piperidine derivatives of Formula IV with suitable carboxylic acid chlorides of formula $R^{11}$-COCl in the presence of base (potassium carbonate or triethylamine). When $R^{11}$-$CH_2$ designates a group of formula -D-B-A-R the corresponding carboxylic acid chlorides of formula $R^{11}$-COCl are either commercially available or prepared according to standard procedures.

When $R^{11}$-$CH_2$ designates a group of Formula II the corresponding carboxylic acid chlorides of Formula XII,

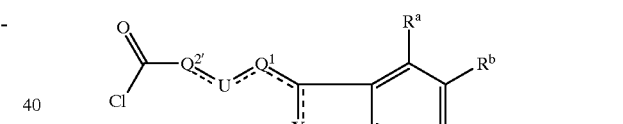

wherein $R^a$–$R^d$, X, Y, U, and $Q^1$ are as previously defined and $Q^{2'}$ is such a group that $Q^{2'}$-$CH_2$ is a group $Q^2$ as previously defined, are prepared from the corresponding carboxylic acids by known methods.

The piperidine derivatives of Formula IV where $Z^1$ and $Z^2$ are linked together, are prepared as follows:

Spiro[isobenzofuran-1(3H),4'-piperidine] according to the method described by Marxer et al, *J. Org. Chem.* 1975, 40, 1427.

2,3-Dihydro-spiro[1H-indene-1,4'-piperidine] and 3,4-dihydro-spiro[naphtalene-1(2H)-4'-piperidine] according to the method described in French Patent. No. 1,335,831.

1'-Methyl-spiro[benzo[c]thiophene-1(3H),4'-piperidine] according to the method described by Parham et al, *J. Org. Chem.* 1976. 41, 2628. The corresponding demethylated derivative was obtained by treatment with ethyl chloroformate followed by alkaline hydrolysis of the intermediary ethyl carbamate.

1'-Phenylmethyl-spiro[1 H-2-benzopyran-4(3H),4'-piperidine] according to the method described by Yamamoto et al, *J. Med. Chem.*, 1981, 24, 194. The corresponding debenzylated derivative is obtained by hydrogenation in the presence of a palladium catalyst.

3,4-Dihydro-1'-phenylmethyl-spiro[2H-1-benzopyran-2, 4'-piperidine] according to the method described by Yamamoto et al, *Chem. Pharm. Bull.* 1981, 29, 3494. The corresponding debenzylated derivative is obtained by treatment with ethyl chloroformate followed by alkaline hydrolysis of the intermediary ethyl carbamate.

1'-Phenylmethyl-spiro[2H-1-benzopyran-2,4'-piperidine] is obtained according to the method described by Yamamoto et al, *Chem. Pharm. Bull.* 1981, 29, 3494. The corresponding debenzylated derivative is obtained by hydrogenation in the presence of a palladium catalyst.

1'-Phenylmethyl-spiro[3H-2-benzopyran-3,4'-piperidine]-1(4H)-one according to the method described by Yamamoto et al, *J. Med. Chem.* 1981, 24,194. Reduction with lithium aluminium hydride followed by treatment with phosphoric acid according to the procedure described by Marxer et al, *J. Org. Chem.* 1975, 40, 1427 yields 1,4-dihydro- 1'-phenylmethyl-spiro[3H-2-benzopyran-3,4'-piperidine] which is debenzylated by hydrogenation in the presence of a palladium catalyst.

1'-Benzylspiro[4H-1-benzopyran-4,4'-piperidine] is obtained by a method: analogously to the method described in EP 0 414 289 A1 for the synthesis of 1'-benzyl-1,4-dihydrospiro[naphtalene-1,4'-piperidine]. Hydrogenation in the presence of a palladium catalyst gave 2,3-dihydrospiro (4H-1-benzopyran-4,4'-piperidine].

Spiro[1,3-benzodioxole-2,4'-piperidine] is obtained by refluxing 1-ethoxycarbonyl-4-piperidinone and catechol in toluene solution in the presence of P-toluenesulfonic acid with continous removal of water followed by removal of the benzyl group by hydrogenation in the presence of a palladium catalyst.

The substituents $R^2$–$R^7$ are introduced by applying suitably substituted starting compounds to methods analogously to the above mentioned.

The piperidine derivatives of Formula IV where $Z^1$ and $Z^2$ are not linked are prepared by known methods, see e.g. U.S. Pat. No. 2,891,066; McElvain et at *J. Amer. Chem. Soc.* 1950, 72, 3134; Bally et al *Chem.Ber.* 1887, 20, 2590.

Alkylation of a compound of Formula IV according to method b) is conveniently performed in an inert organic solvent such as a suitably boiling alcohol or ketone, preferably in the presence of a base (potassium carbonate or triethyl amine) at reflux temperature.

The alkylating reagents of formula $R^1$-V where $R^1$ designates -D-B-A-R wherein A is O, S, or a bond and D, B, and R are as previously defined, are prepared by standard literature methods. The corresponding sulfoxides and sulfones are obtained by oxidation of the sulfides according to methods well known in the art.

Such alkylating agents in which A represents a group

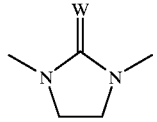

wherein W is O or S are prepared by the method disclosed in DE-OS No 2035370.

The preparations of alkylating reagents of formula $R^1$-V where $R^1$ designates a group having the general Formula II are illustrated by examples in the following reaction schemes. In the formulas of the reaction schemes $R^a$–$R^d$, V and Ar are as previously defined, and E designates a 1-piperidyl group of general Formula IV. Indenes of Formula II are conveniently prepared according to Scheme 1, in which $R^a$–$R^d$ and V are as previously defined.

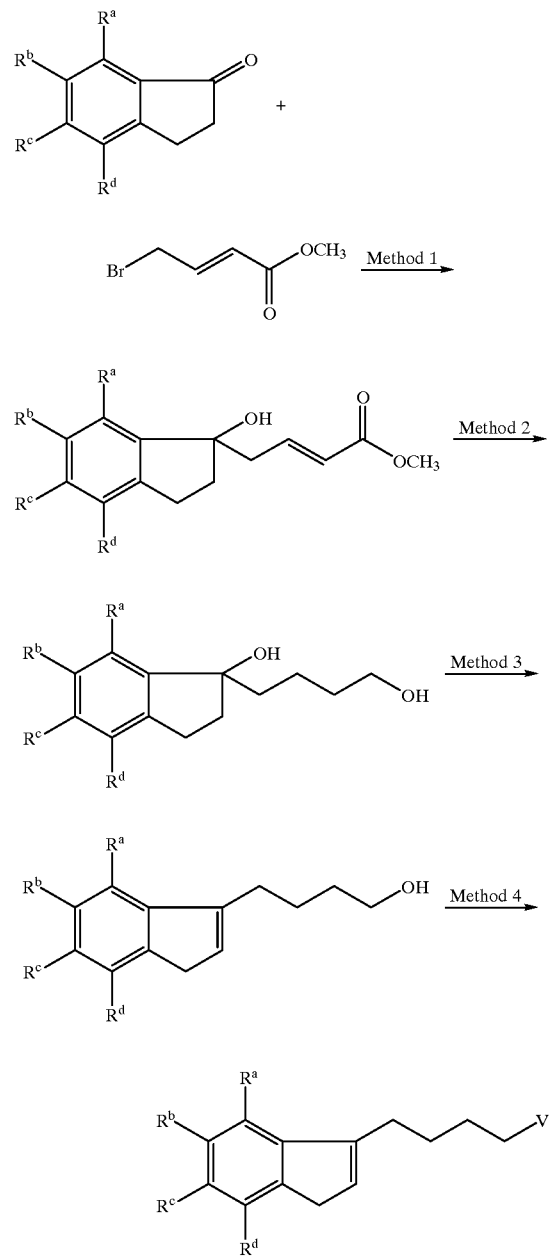

Scheme 1

Method 1 is a conventional Reformatsky condensation performed with activated zinc. Method 2 consists of a lithium aluminium hydride reduction performed in an inert organic solvent such as diethyl ether or tetrahydrofuran at reflux temperature.

The elimination in Method 3 is preferably performed in a suitable alcohol, e.g. methanol, in the presence of a strong mineral acid, e.g. concentrated hydrochloric acid. Preferably, Method 4 is treatment with methanesulfonyl chloride in the presence of triethyl amine in dichloromethane, thus giving the corresponding methanesulfonate, but may alternatively be conversion of the hydroxy group to a halogen by means of a suitable reagent, e.g. thionyl choride.

Indanes of Formula 11 are prepared according to Scheme 2, in which $R^a$–$R^d$ and V are as previously defined.

Scheme 2

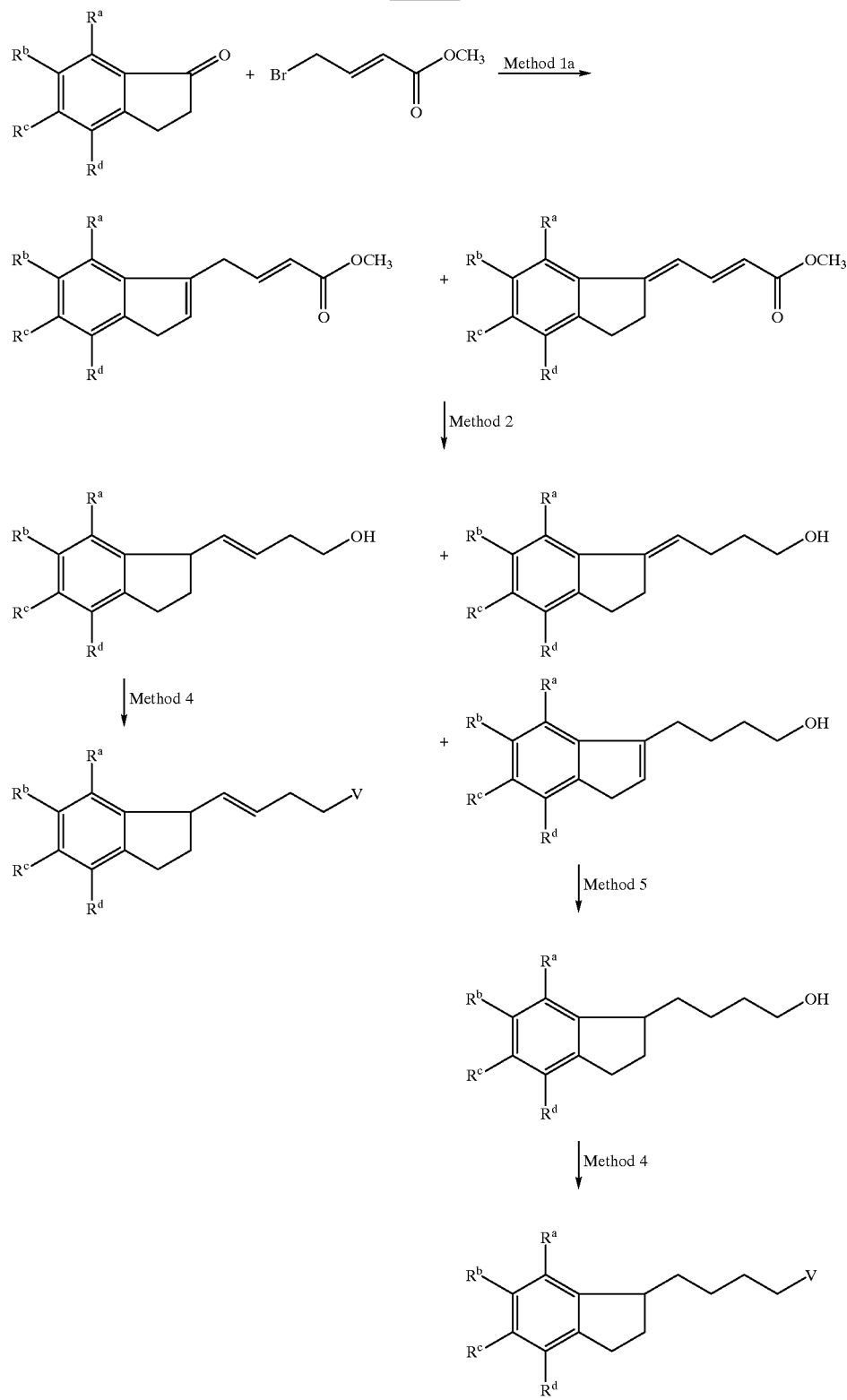

Method 1a is analogous to Method 1 with the modification that elimination of water is performed directly on the crude product by means of concentrated hydrochloric acid. The mixture of isomers obtained is reduced according to Method 2. One of the isomers obtained is isolated while the remaining mixture is hydrogenated in a conventional Parr apparatus (Method 5) in the presence of a suitable noble metal catalyst. e.g. palladium or platinum.

Indoles of Formula II are most conveniently prepared either from indole alkanoic acid, exemplified by indole butanoic acid as described in Eur. Pat. Appl. No. 376607, or according to Scheme 3, in which $R^a$–$R^d$, Ar and V are as previously defined.

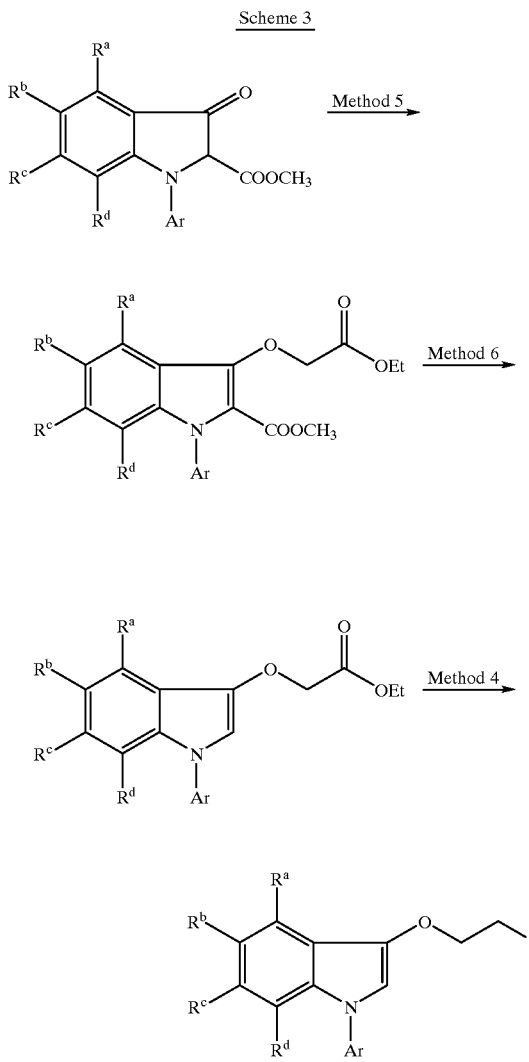

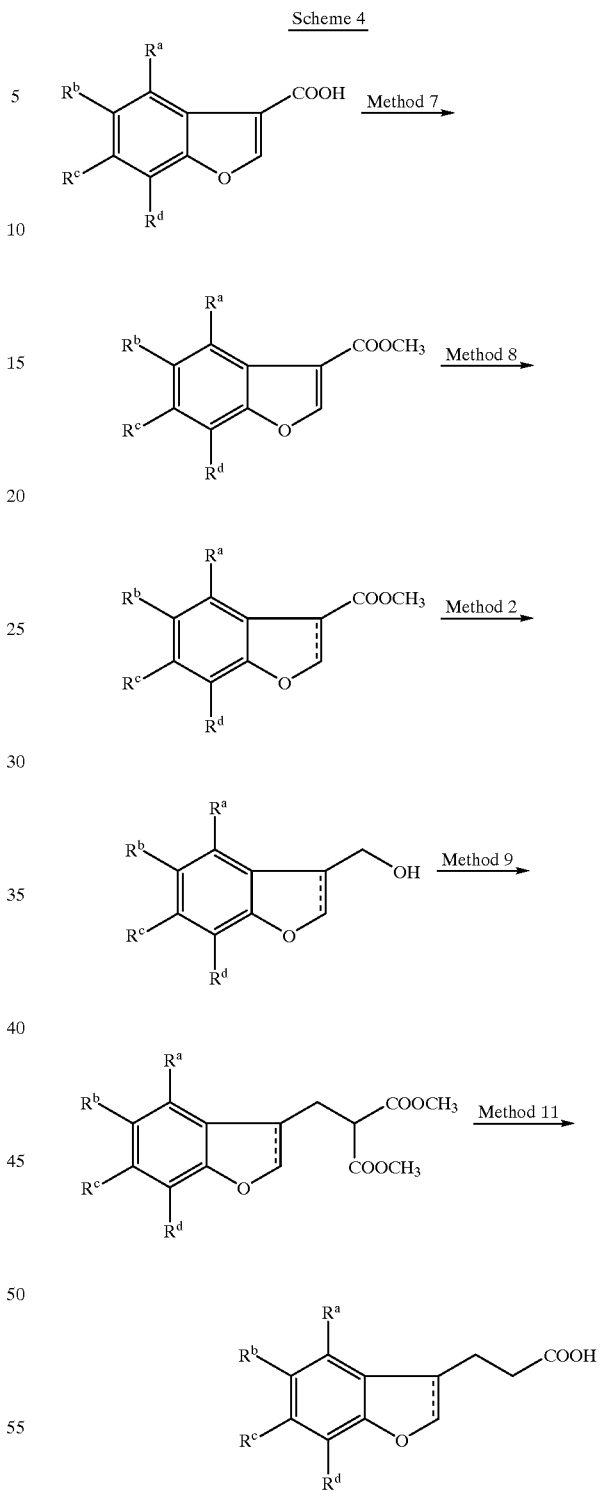

The starting indoxyl ester is prepared by the method described in U.S. Pat. No. 4,710,500 and references therein. The alkylation in Method 5 is performed in an inert, suitably boiling, organic solvent, e.g. an alcohol or a ketone, preferably in the is presence of a base (potassium carbonate or triethyl amine). The decarboxylation in Method 6 is preferably performed thermally, after hydrolysis of the diester to the diacid, in a suitable inert solvent, e.g. quinoline, dimethyl formamide, or N-methyl-2-pyrrolidinone (NMP) in the presence of copper.

Indol-3-yloxypropyl derivatives can also be obtained by heating a mixture of 3-acetoxyindoles and 1,3-propylene glycol in the presence of sulfuric acid, thereby obtaining 3-(indol-3-yloxy)-1-propanol derivatives which are converted to the corresponding methanesulfonates or halides by Method 4.

Benzofuranes and 2,3-dihydrobenzofuranes of Formula II are prepared according to Schemes 4 and 5, in which $R^a$–$R^d$ and E are as previously defined.

Method 7 is a conventional conversion to the methyl ester by treating the carboxylic acid with thionyl chloride followed by addition of methanol to the intermediate carboxylic acid chloride. The 2,3-dihydrobenzoturanes are obtained by reduction with magnesium (Method 8) at this stage, while the benzofuranes are obtained by skipping this step. Method 9 consists of conversion of the alcohol group to the corresponding chloride by means of thionyl chloride followed by treatment with dimethyl malonate in a suitable solvent, e.g.

NMP, in the presence of base, preferably potassium tert-butoxide. Method 11 is similar to Method 6 except the decarboxylation is performed without addition of copper.

Benzo[b]thiophene-S,S-dioxide derivatives are obtained by oxidation of the corresponding benzo[b]thiophene derivatives according to standard literature methods. 2,3-

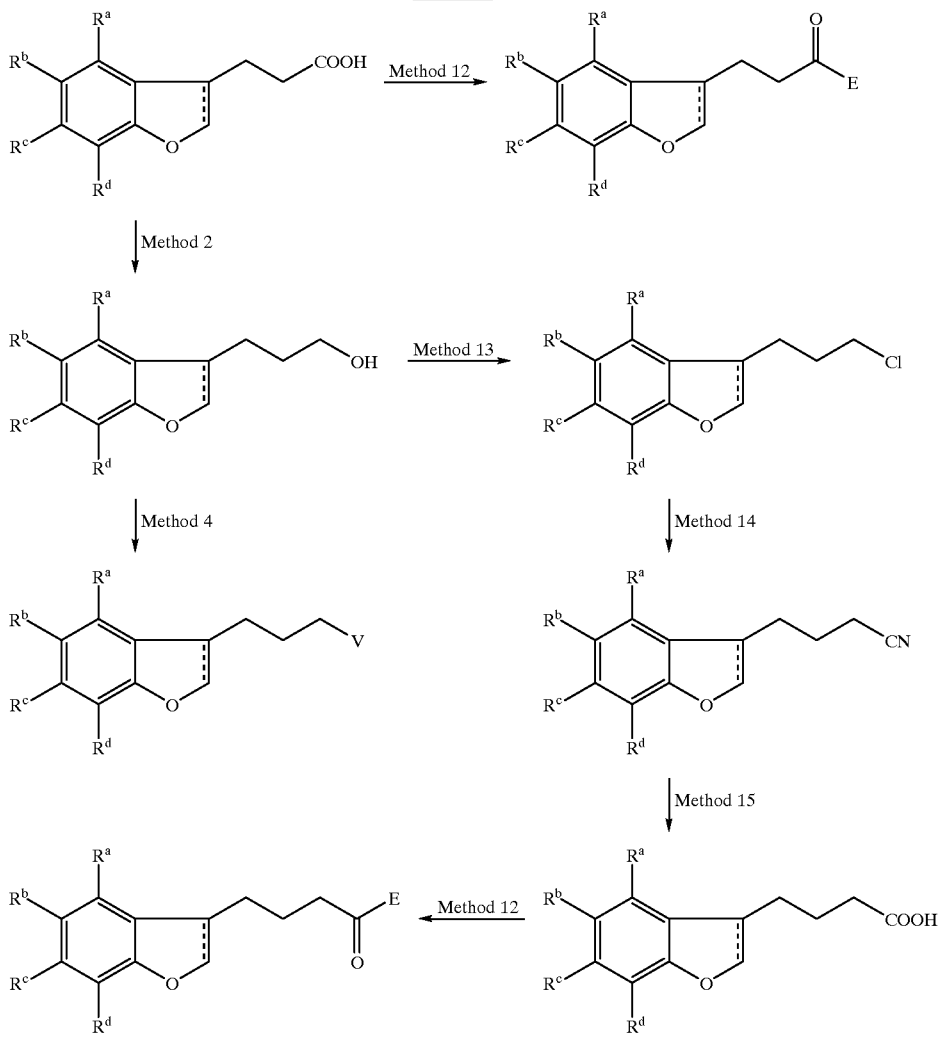

Scheme 5

Method 12 consists of a conventional conversion of the carboxylic acid to the amide via the carboxylic acid chloride. Prolongation of the side chain is accomplished by conversion of the hydroxy group to the chloride by treatment with preferably thionyl chloride in dichloromethane in the presence of a few drops of dimethyl formamide (Method 13) followed by treatment with a cyanide salt, e.g. potassium cyanide, in a suitable aprotic dipolar solvent, preferably dimethyl sulfoxide, at 100–200° C. (Method 14). Hydrolysis of the cyano group is accomplished with mineral acid at, elevated temperature (Method 15). ;

Benzo[b]thiophenes and 2,3-dihydrobenzo[b]thiophenes of Formula II are prepared by methods analogous to the methods described in Schemes 4 and 5. Benzo[b]thiophen-3-ylmethyloxyethyl derivatives are prepared from methyl benzo[b]thiophene-3-carboxylate by reduction to the methanol derivative with lithium aluminium hydride followed by alkylation with ethyl bromoacetate and subsequent reduction to benzo[b]thiophen-3-ylmethyloxyethanol derivatives which are converted to the target compounds via Method 4. Benzofuran-3-ylmethyloxyethyl derivatives are prepared analogously.

Dihydroindoles of Formula 1I are prepared by methods analogous to method d). indolones of Formula 11 are prepared by methods analogous to method e). Indazoles of Formula II are prepared by methods analogous to method j).

Reductive alkylation of amines of Formula IV according to method c) is performed by standard literature procedures. The aldehydes, carboxylic acids, and ketones of formulas $R^{11}$-CHO, $R^{11}$-COOH, and $R^{12}$-CO-$R^{13}$, respectively, are either commercially available or are prepared according to standard procedures or according to methods analogous to the methods described in Schemes 1–5.

Reduction of the C=$Y^1$ double bond according to method d) is conveniently performed by catalytic hydrogenation in an alcohol with a platinum catalyst or by hydrogenation with diborane or a diborane precursor such as trimethyl amine or dimethyl sulfide complex in tetrahydrofuran or dioxane from 0° C. to reflux temperature, followed by acid catalyzed hydrolysis of the intermediate borane derivative.

Alternatively, the double bond can be reduced by sodium borohydride in methanol in the presence of trifluoroacetic acid (see e.g. Berger et al. J. Med. Chem. 1977, 20, 600).

Oxidation of a compound of Formula VI according to method d, is performed according to Szabo-Pustay et al., *Synthesis,* 1979, 276.

Alkylation, acylation or sulfonylation of compounds of Formula VIII according to methods f), h) and i), respectively, are performed in an inert solvent such as a suitably boiling alcohol or ketone, preferably in the presence of a base (potassium carbonate or triethyl amine). The alkylating reagents $R^{10'}$-$V^1$, the acylating reagents $R^{10''}$-CO-$V^1$, $R^{10'}$-CO-$V^1$, and Ar-CO-$V^1$, and the sulfonylation reagents $R^{10'}$-$SO_2$-$V^1$, and Ar-$SO_2$-$V^1$ respectively, are commercially available or are prepared by standard procedures.

Arylation of a compound of Formula VIII according to method g) is most conveniently performed by applying the well known Ullmann reaction. The arylating reagents Ar-$V^1$ are commercially available.

Reductive alkylation of compounds of Formula VIII according to method j) are performed by standard literature methods.

The ring closure of compounds of Formula IX according to method k) is most conveniently performed by heating a compound of Formula IX in a suitable inert organic solvent such as dimethyl formamide in the presence of a base, preferably potassium tert-butoxide.

Hydrazones of Formula IX are prepared according to Scheme 6, in which $R^a$–$R^d$, $R^{10}$ and Hal are as previously defined.

presence of a hydrazine. Alternatively, the hydroxy derivative resulting from Method 16 may be converted to the amine via the corresponding mesylate analogous to Method 4 and a) before conversion of the keto group.

The reduction according to method 1) is most conveniently performed by catalytic hydrogenation in an alcohol with a platinum catalyst. Compounds of Formulas V, VI, and VIII are prepared by methods a), b), j), k), or l). Compounds of Formula XI are prepared by treating a compound of formula $R^1$–$V^1$ with a 4-aryl-pyridine in a suitably boiling alcohol.

In the following the invention is further illustrated by examples which, however, may not be construed as limiting:

EXAMPLE 1

1'-Butylspiro[isobenzofuran-1(3H),4'-piperidine], oxalate, 1a.

A mixture of spiro[isobenzofuran-1(3H),4'-piperidine] (2 g), n-butyl bromide (4 g), potassium carbonate (5 g), and potassium iodide (0.2 g) in 100 ml of 4-methyl-2-pentanone was refluxed for 16 h. After cooling the reaction mixture was washed with 100 ml of water and concentrated in vacua. The title compound crystallized as the oxalate salt from acetone by addition of oxalic acid. Recrystallized from an ethanol/ether mixture. Yield: 1.2 g, mp: 171–73° C.

In a similar manner was also prepared:

1'-Pentylspiro[isobenzofuran-1(3H),4'-piperidine], oxalate, 1b, mp: 170–72° C.

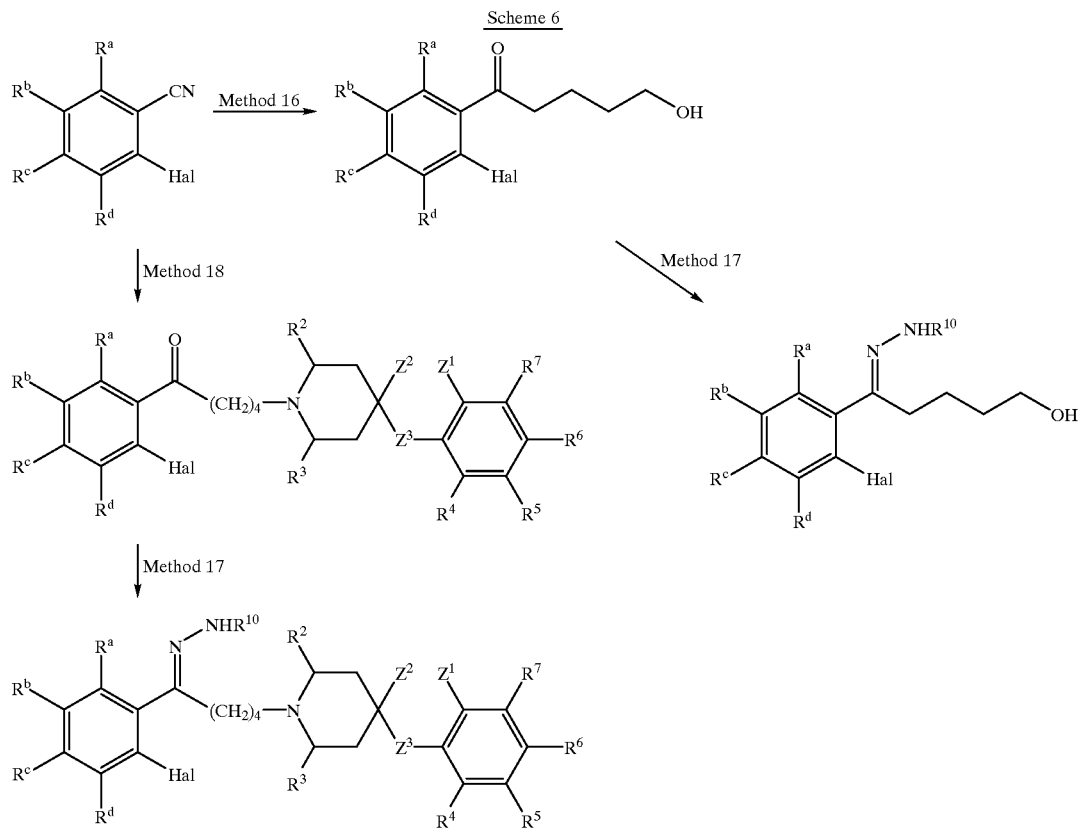

Scheme 6

Method 16 is an addition of the Grignard reagent of 4-chloro-1-butanol to o-halobenzonitriles under standard conditions for Grignard reactions Conversion to the hydrazone (Method 17) is accomplished by reflux in ethanol in the

EXAMPLE 2

1'-(4-Phenyl-1-butyl)spiro[isobenzofuran-1(3H),4'-piperidine], fumarate, 2a

To an ice cooled solution of 4-phenyl-1-butanol (20 g) and triethyl amine (15 g) in 200 ml of dichloromethane, a solution of methanesulfonyl chloride (12 ml) in 50 ml of dichloromethane was added dropwise. After stirring for 1 h at 10° C. the reaction mixture was washed with water. Extraction of the water phase with dichloromethane, drying of the combined organic phases over $MgSO_4$ followed by removal of the volatile components in vacua, gave 29 g of a slightly yellow oil, 4-phenyl-1-butyl methanesulfonate, which was sufficiently pure for use in the next step. A mixture of spiro[isobenzofuran-1(3H),4'-piperidine] (2 g), 4-phenyl-1-butyl methanesulfonate (6 g) and potassium carbonate (14 g) in 75 ml of 4-methyl-2-pentanone was refluxed for 20 h. After cooling the reaction mixture was filtered and concentrated in vacuo. The remaining viscous oil was applied to a silica gel column (eluent: ether/methanol/triethyl amine 93:5:2) giving a colorless oil which crystallized as the fumarate salt, 2a. from acetone by addition of fumaric acid. Yield: 0.7 g, mp: 197–99° C.

In a similar manner were also prepared:
1'-(4-Cyclohexyl-1-butyl)spiro[isobenzofuran-1(3H), 4'-piperidine), oxalate, 2b, mp: 139–42° C.
2,3-Dihydro-1'-(4-phenyl-1-butyl)spiro[1H-indene-1,4'-piperidine], fumarate, 2c, mp: 207–11° C.
1'-(4-Phenyl-1-butyl)spiro[benzo[c]thiophene-1(3H),4'-piperidine], maleate, 2d, mp: 176–77° C.
3,4-Dihydro-1'-(4-phenyl-1-butyl)spiro[naphtalene-1(2H), 4'-piperidine], fumarate, 2e, mp: 191–93° C.
1'-(4-Phenyl-1-butyl)spiro[1H-2-benzopyran-4(3H),4'-piperidine], maleate, 2f, mp: 169–70° C.
1,4-Dihydro-1'-(4-phenyl-1-butyl)spiro[3H-2-benzopyran-3,4'-piperidine], maleate, 2g, mp: 152–53° C.
3,4-Dihydro-1'-(4-phenyl-1-butyl)spiro[2H-1-benzopyran-2,4'-piperidine], oxalate, 2h, mp: 155–57° C.
1'-(4-Phenyl-1-butyl)spiro[2H-1-benzopyran-2,4'-piperidine], fumarate, 2i, mp: 184–85° C.
1'-(3-Cyclohexyloxy-1-propyl)spiro[isobenzofuran-1(3H), 4'-piperidine], fumarate, 2j, mp: 154–55° C.
1'-(3-Phenoxy-1-propyl)spiro[isobenzofuran-1(3H),4'-piperidine], 2k, mp: 143–44° C.
1'-(3-Phenoxy-1-propyl)spiro[3H-2-benzopyran-3,4'-piperidine], maleate, 2l, mp: 171–73° C.
1'-(3-Adamantyloxy-1-propyl)spiro[3H-2-benzopyran-3,4'-piperidine], maleate, 2m, mp: 221–24° C.
1'-(3-Methylthio-1-propyl)spiro[isobenzofuran-1(3H),4'-piperidine], oxalate, 2n, mp: 126–27°.
1'-(3-Cyclohexylthio-1-propyl)spiro[isobenzofuran-1(3H), 4'-piperidine], oxalate, 2o, mp: 170–74° C.
1'-(3-Phenylthio-1-propyl)spiro[isobenzofuran-1(3H),4'-piperidine], oxalate,2p, 152–55° C.
1'-(3-Methylsulfonyl-1-propyl)spiro[isobenzofuran-1(3H), 4'-piperidine], 2q, mp: 163–64° C.
1'-(3-Cyclohexylsulfonyl-1-propyl)spiro[isobenzofuran-1(3H),4'-piperidine], 2r. mp: 118–20° C.
1'-(3-Phenylsulfonyl-1-propyl)spiro[isobenzofuran-1 (3H), 4'-piperidine], 2s, mp: 197–202° C.
8'-(4-Phenyl-1-butyl)spiro[isobenzofuran-1(3H),3'-8-azabicyclo[3,2,1]octane], maleate, 2t, mp: 180–81° C.
1'-[4-(3-Indolyl)-1-butyl]-spiro[isobenzofuran-1(3H),4'-piperidine], 2u, mp: 150–55° C.
1'-[4-(3-Indolyl)-1-butyl]-spiro[1H-2-benzopyran-4(3H),4'-piperidine], oxalate, mp: 222–25° C.
1'-[5-(3-Indolyl)-1-pentyl]-spiro[1H-2-benzopyran-4(3H), 4'-piperidine], oxalate, 2x, mp: 145–46° C.
1'-[6-(3-Indolyl)-1-hexyl]-spiro[1H-2-benzopyran-4(3H),4'-piperidine], oxalate, 2y, mp: 117–18° C.
1'-[4-(5,6-Dichloro-3-indolyl)-1-butyl]-spiro[isobenzofuranr-1(3H), 4'-piperidine], 2z, mp: 122–23° C.
1'-4-(5-Fluoro-3-indolyl)-1-butyl]-spiro[isobenzofuran-1 (3H),4'-piperidine], 2aa, mp: 185–87° C.
1'-[4-(1-Methyl-3-indolyl)-1-butyl]-spiro[isobenzofuran-1 (3H),4'-piperidine], 2bb, mp: 101–2° C.
3-[4-(4-Phenyl-1-piperidyl)-1-butyl]indole, 2cc, mp: 131–32° C.
3-[4-(4-(3,4-Dichlorophenyl)-1-piperidyl)-1-butyl]indole, 2dd, mp: 118–19° C.
5,6-Dichloro-3-[4-(4-(4-fluorophenyl)-1-piperidyl)-1-butyl]-indole, 2ee, mp: 120–21° C.
3-[6-(4-(4-Fluorophenyl)-1-piperidinyl)-1-hexyl]indole, 2ff, mp: 90–91° C.
3-[4-(4-(2-Methoxyphenyl)-1-piperidinyl)-1-butyl]indol, oxalate, 2gg, mp: 183–88° C.
1'-[4-(1-Benzyl-3-indolyl)-1-butyl]-spiro[isobenzofuran-1 (3h),4'-piperidine], 2hh, mp: 166–68° C.
3-[4-(4-(4-Fluorophenyl)- 1-piperidyl)-1-butyl]indol-2-one, 2ii, mp: 108–10° C.
6-Fluoro-1'-(4-(3-indolyl)-1-butyl)spiro[isobenzofuran-1 (3H),4'-piperidine], 2jj, mp: 189–91° C.

EXAMPLE 3

1'-(4-(3-Cyclohexylimidazolidin-2-on-1-yl)- 1-butyl)spiro [isobenzofuran-1 (3H), 4'-piperidine], hydrochloride, 3a.

A mixture of 1-cyclohexyl-3-(4-chloro-1-butyl)-2-imidazolidinon (2.0 g, prepared according to the method described in Ger. Offen. 2035370), spiro[isobenzofuran-1 (3M,4'-piperidine] (1.5 g), potassium carbonate (4.4 g), and potassium iodide (0.1 g) in 60 ml of methyl isobutyl ketone was refluxed for 17 h. After cooling to room 10 temperature the mixture was filtered and the solvent removed in vacuo. The remaining oil was purified by column chromatography (silica gel, eluent: ethyl acetate/heptane/triethyl amine= 9:1:1). The title compound crystallized as the hydrochloride from an acetone/ether mixture by addition of en etheral solution of HCl. Yield: 1.9 g, mp: 203–7° C.

In a similar manner were also prepared:
1'-(2-(3-Phenylimidazolidin-2-on-1-yl)-1-ethyl)spiro [isobenzofuran-1(3,4'-piperidine], hydrochloride, 3b, mp: 151–54° C.
1'-(3-(3-Phenylimidazolidin-2-on-1-yl)-1-propyl)spiro [isobenzofuran-1(3H,4'-piperidine], hydrochloride, 3c, mp: 232–50° C.
1'-(2-(3-Cyclohexylimidazolidin-2-on-1-yl)-1-ethyl)spiro [isobenzofuran-1(3H),4'-piperidine), hydrochloride, 3d, mp: 160–61° C.

EXAMPLE 4

1'-Propyl-spiro[isobenzofuran-1(3H),4'-piperidine], maleate, 4a.

To a mixture of spiro[isobenzofuran-1(3 H),4'-piperidine] (3 g), potassium carbonate (5 g), and 100 ml of water in 100 ml of toluene, propionyl chloride (3 g) was added dropwise. After stirring for 3 h at room temperature the toluene phase was separated, washed with water and concentrated in vacuo. The remaining oil was dissolved in 100 ml of tetrahydrofuran and lithium aluminium hydride (1 g) was added. After 3 h of reflux the reaction mixture was cooled and, successively, water (2 ml), 9 N NaOH (1 ml), and water (5 ml) was added. The mixture was filtered and concentrated in vacuo and the titel compound crystallized as the maleate salt, 4a, from ethyl acetat by addition of maleic acid. Recrystallized from an acetone/ether mixture. Yield: 0.7 g, mp: 107–9° C.

In a similar manner were also prepared:
1'-(5-Methyl-1-hexyl)-spiro[isobenzofuran-1(3H),4'-piperidine), oxalate, 4b, mp: 162–64° C.
1'-(2-Phenyl-1-ethyl)-spiro[isobenzofuran-1(3h),4'-piperidine], maleate, 4c, mp: 161–63° C.
1'-(3-Phenyl-1-propyl)-spiro[isobenzofuran-1(3H),4'-piperidine], maleate, 4d, mp: 142–44° C.
1'-(5-Phenyl-1-pentyl)-spiro[isobenzofuran-1 (3h),4'-piperidine], oxalate, 4e, mp: 115–17° C.
1'-(6-Phenyl-1-hexyl)-spiro[isobenzofuran-1 (3H),4'-piperidine], oxalate, 4f, mp: 156–57° C.
1'-Octadecanyl-spiro[isobenzofuran-1(3H),4'-piperidine], oxalate, 4g, mp: 208–10° C.

EXAMPLE 5

1'-[4-[1-(4-Fluorophenyl)-3-indolyl]-1-butyl]-spiro[isobenzofuran-1 (3h),4'-piperidine], 5a.

A mixture of 2u (3 g), 1-fluoro-4-iodobenzene (5 g), copper powder (0.5 g), and potassium carbonate (2 g) in 50 ml of NMP was kept at 160–170° C. for 5 h. After filtration, water was added followed by extraction with ether. Removal of solvent in vacuo gave a red oil which was applied to a silica gel column (eluent: ethyl acetate). The title compound, 5a, crystallized as the oxalate salt from acetone by addition of oxalic acid. Yield: 1.3 g, mp: 169–70° C.

In a similar manner were also prepared:
1,4-Dihydro-1'-[4-[1-(4-Fluorophenyl)-3-indolyl]-1-butyl]spiro[3H-2-benzopyran-3,4'-piperidine], maleate, 5b, mp: 142–43° C.
1'-(4-(1-(3-Thienyl)-3-indolyl]-1-butyl]spiro[isobenzofuran-1(3H),4'-piperidine]5c, mp: 182–83° C.
1'-[4-[1-(2-Thienyl)-3-indolyl]-1-butyl]spiro[isobenzofuran-1(3H),4'-piperidine], 5d, mp: 198–202° C.
1'-[4-[1-(3-Furanyl)-3-indolyl]-1-butyl]spiro[isobenzofuran-1(3H),4'-piperidine], 5e, mp: 141–42° C.
1-(4-Fluorophenyl)-3-[4-(4-phenyl-1-piperidyl)-1-butyl]indole, oxalate, 5f, mp: 171–73° C.
1'-[4-[1-(4-Pyridyl)-3-indolyl]-1-butyl]spiro[isobenzofuran-1(3H),4'-piperidine], oxalate, 5g, mp: 127–29° C.

EXAMPLE 6

1'-(4-(1-Methanesulfonyl-3-indolyl)-1-butyl)spiro[isobenzofuran-1(3 H),4'-piperidine], oxalate, 6a.

A solution of NaOH (20 g) in water (20 ml) was cooled to 10° C. and a solution of 4-(3-indolyl)-1-butanol (4 g) in methylene chloride (60 ml) was added together with tetrabutylammonium hydrogensulfate (0.8 g). Methanesulfonyl chloride (2.5 ml) in methylene chloride (25 ml) was added dropwise at 15° C. followed by stirring for 20 min. at room temperature. The phases were separated and the organic phase washed with water. Drying over magnesium sulfate and removal of solvent in vacuo gave an oil which was purified by column chromatography (silica gel, eluent: ether/methylene chloride/heptane =1:1:1) giving 1.8 g of a heavy oil, 4-(1-methanesulfonyl-3-indolyl)-1-butyl methanesulfonate which was converted to the title compound by the method described in EXAMPLE 2. The oxalate salt crystallized from acetone by addition of oxalic acid. Yield: 1.0 g. mp: 83–85° C.

In a similar manner were also prepared:
1'-(4-(1-p-Toluenesulfonyl-3-indolyl)-1-butyl)spiro[isobenzofuran-1(3H),4'-piperidine], oxalate, 6b, mp: 201–4° C.
6-Fluoro-1'-(4-(1-(2-thienyl)sulfonyl-3-indolyl)-1-butyl)spiro[isobenzofuran-1(3H),4'-piperidine), oxalate, 6c, mp: 184–86° C.

EXAMPLE 7

1'-(4-(1-Acetyl-3-indolyl)-1-butyl)spiro[isobenzofuran-1(3H),4'-piperidine], oxalate, 7.

A solution of acetyl chloride (0.8 ml) in methylene chloride (10 ml) was added dropwise at 15° C. to a mixture of 2u (1.8 g), sodium hydroxide (1 g), and tetrabutylammonium hydrogensulfate (0.2 g) in methylene chloride (40 ml). After stirring for 1 h at room temperature water was added, the organic phase separated and dried over magnesium sulfate. Filtration and removal of solvent in vacuo gave a viscous oil which was purified by column chromatography (silica gel, eluent: heptane/ethyl acetate/triethyl amine= 60:40:4). The title compound crystallized as the oxalate salt from acetone by addition of oxalic acid. Yield: 0.45 g, mp: 139–40° C.

EXAMPLE 8

1'-[3-[1-(4-Fluorophenyl)-3-indolyloxy]-1-propyl]spiro[isobenzofuran-1(3H),4'-piperidine], oxalate, 8a.

A mixture of 3-acetyloxy-1-phenylindole (24 g), 1,3-dihydroxypropane (240 ml), and conc. sulfuric acid (10 ml) was heated to 80° C. for 2 h. Water was added followed by extraction with ether. The ether phase was dried over magnesium sulfate followed by removal of solvent in vacuo giving 3-(1-phenyl-3-indolyloxy)-1-propanol, sufficiently pure for use in the next step.

The title compound was obtained by the method described in EXAMPLE 2 using spiro[isobenzofuran-1(3H),4'-piperidine] and crystallized as the oxalate salt from acetone by addition of oxalic acid. Yield: 2 g, mp: 151–54° C.

In a similar manner were also prepared:
1'-[3-[6-Chloro-1-(4-fluorophenyl)-3-indolytoxy)-1-propyl]spiro[isobenzofuran-1(3M),4'-piperidine], oxalate, 8b, mp: 180–81 ° C.
1'-[3-[5-Chloro-1-(4-fluorophenyl)-3-indolyloxy]-1-propyl]spiro[isobenzofuran-1(3H,4'-piperidine], oxalate, 8c, mp: 1 15–18° C.
5-Chloro-1-(4-fluorophenyl)-3-[3-(4-(4-methylphenyl)-1-piperidinyl)-1-propyloxy]indol, 8d, mp: 111–12° C.

EXAMPLE 9

1'-[4-[1-(4-Fluorophenyl)-3-indolyl]- 1-butyl]spiro[1H-2-benzopyran-4(3H), 4'-piperidine], maleate, 9a.

A tetrahydrofuran solution (500 ml) of methyl 4-(3-indolyl)-butyrate (103 g) was added dropwise to a suspension of lithium aluminium hydride (25 g) in tetrahydrofuran (1000 ml) at 40° C. followed by stirring for 1 h at room temperature. Usual work-up gave 4-(3-indolyl)-1-butanol (96 g) as an oil. Arylation with 1-fluoro-4-iodobenzene according to the method described in EXAMPLE 5 yielded 4-[1-[4-fluorophenyl)-3-indolyl]-1-butanol which was converted to the title compound 9a by the method described in EXAMPLE 2 using spiro[1 H-2-benzopyran-4(3H),4'-piperidine]. The maleate salt crystallized from acetone by addition of maleic acid. Yield: 1.5 g, mp: 189–90° C.

In a similar manner were also prepared:
1'-[4-[5-Fluoro-1-(4-fluorophenyl)-3-indolyl]-1-butyl]spiro[isobenzofuran-1 (3H), 4'-piperidine], oxalate, 9b, mp: 164–65° C.
1'-[4-[1-(4-fluorophenyl)-3-indolyl]- 1-butyl]spiro[benzo[c]thiophene-1(3H), 4'-piperidine], maleate, 9c, mp: 179–80° C.
8'-[4-[1-(4-Fluorophenyl)-3-indolyl]-1-butylspiro[isobenzofuran-1(3H),3'-8-azabicyclo[3,2,1octane], maleate, 9d. mp: 161–62° C.
6-Fluoro-1'-[4-[1-(4-fluorophenyl)-3-indolyl]-1-butyl]spiro[isobenzofuran-1(3H),4'-piperidine], hydrochloride, 9e, mp: 227–31° C.

1'-[4-[ -(4-Fluorophenyl)-3-indolyl]-1-butyl]-6-isopropylspiro[isobenzofuran-1(3H), 4'-piperidine], oxalate, 9f, mp: 129–44° C.

7-Fluoro-1'-[4-[1-(4-fluorophenyl)-3-indolyl]-1-butyl]spiro[isobenzofuran-1(3H), 4'-piperidine], oxalate, 9g, mp: 186–89° C.

1'-[4-[1-(4-Fluorophenyl)-3-indolyl]-1-butyl]-5-methylspiro[isobenzofuran-1(3H),4'-piperidine], oxalate, 9h, mp: 154–56° C.

1'-(4-(1-(4-Methylphenyl)-3-indolyl]-1-butyl]spiro[1H-2-benzopyran-4(3H), 4'-piperidine], fumarate, 9i, mp: 186–88° C.

1'-[4-[5-Fluoro-1-(3-thienyl)-3-indolyl]-1-butyl]-spiro[isobenzofuran-1(3H),4'-piperidine], fumarate, 9j, mp: 184–86° C.

1'-[4-[1-(3-Pyridinyl)-3-indolyl]-1-butyl]spiro[1H-2-benzopyran-4(3H), 4'-piperidine],fumarate, 9k, mp: 185–87° C.

1-(4-Fluorophenyl)-3-[4-(4-(4-fluorophenyl)-1-piperidyl)-1-butyl]indole, oxalate, 9l, mp: 190–91° C.

1-(4-Fluorophenyl)-3-[4-(4-(4-methylphenyl)-1-piperidyl)-1-butyl]indole, maleate, 9m, mp: 130–32° C.

1-(4-Fluorophenyl)-3-[4-(4-(4-isopropylphenyl)-1-piperidyl)-1-butyl]indole, maleate, 9n, mp: 160–62° C.

1-(4-Fluorophenyl)-3-[4-(4-(4-dimethylaminophenyl)-1-piperidyl)-1-butyl]indole; fumarate, 9o, mp: 180–82° C.

1-Phenyl-3-[4-(4-(4-fluorophenyl)-1-piperidyl)-1-butyl]indole, oxalate, 9p, mp: 174–76° C.

1'-[4-(1-(2-Thiazolyl)-3-indolyl)-1-butyl]spiro[isobenzofuran-1(3H), 4'-piperidine], fumarate, 9q, mp: 165–67° C.

6-Trifluoromethyl-1'-[4-[1-(4-fluorophenyl)-3-indolyl]-1-butyl]spiro[isobenzofuran-1(3H),4'-piperidine], fumarate, 9r, mp: 100–105° C.

4-Fluoro-1'-[4-[1-(4-fluorophenyl)-3-indolyl]-1-butyl]spiro[isobenzofuran-1(3H),4'-piperidine], oxalate, 9s, mp: 160–63° C.

1-(4-Fluorophenyl)-3-[4-(4-(3-trifluoromethylphenyl)-1-piperidyl)-1-butyl]indole, maleate, 9t, mp: 112–13° C.

2,3-Dihydro-1'-[4-[1-(4-fluorophenyl)-3-indolyl]-1-butyl]spiro[4H-1-benzopyran-4,4'-piperidine], oxalate, 9u, mp: 187–92° C.

6-Fluoro-1'-[4-[5-fluoro-1-(4-fluorophenyl)-3-indolyl]-1-butyl]spiro[isobenzofuran-1(H),4'-piperidine], oxalate, 9v, mp: 144–46° C.

EXAMPLE 10

1'-(4-(Benzo[b]thiophen-3-yl)-1-butyl)spiro[isobenzofuran-1(3H),4'-piperidine], maleate, 10a.

A solution of methyl benzo[b]thiophen-3-ylacetate (69 g) in dry tetrahydrofuran (100 ml) was added dropwise to a suspension of lithium aluminium hydride (10 g) in dry tetrahydrofuran (500 ml) at room temperature followed by reflux for 1 h. Hydrolysis with water, filtration and removal of solvent gave an oil which was applied to a silica gel column (eluent: methylene chloride) giving 34.5 g of benzo[b]thiophen-3-ylethanol as an oil.

The product was dissolved in 200 ml of methylene chloride, thionyl chloride (20 ml) was added followed by reflux for 5 h. Removal of solvent and excess thionyl chloride in vacuo gave 3-(2-chloro-1-ethyl)-benzo[b]thiophene as an oil (45 g). The chloride was converted to 4-benzo[b]thiophen-3-yl-1-butanol via treatment with dimethyl malonate followed by hydrolysis, decarboxylation and reduction according to the method described in EXAMPLE 11.

The title compound 10a was prepared from 4-benzo[b]thiophen-3-yl-1-butanol and spiro[isobenzofuran-1(3H),4'-piperidine) by the method described in EXAMPLE 2. Yield: 2.2 g, mp: 144–45° C.

In a similar manner were also prepared:

1,4-Dihydro-1'-(4-(benzo[b]thiophen-3-yl)-1-butyl)spiro[3H-2-benzopyran-3,4'-piperidine], maleate, 10b, mp: 172–73° C.

1'-(4-(5-Methylbenzo[b]thiophen-3-yl)-1-butyl)spiro[isobenzofuran-1(3H),4'-piperidine], maleate, 10c, mp: 164–65° C.

EXAMPLE 11

2,3-Dihydro-5-fluoro-3-[3-(4-(4-fluorophenyl)-1-piperidinyl)-1-propyl]benzofuran, 1a.

To a suspension of 5-fluorobenzofuran-3-carboxylic acid (118 g) in 800 ml of dichloromethane, thionyl chloride (200 ml) and dimethyl formamide (1 ml) were added. After reflux for 3 h the reaction mixture was concentrated in vacuo, and the remaining oil dissolved in 800 ml of dichloromethane. Methanol (1.5 l) was slowly added and the mixture stirred for 1 h. Removal of solvents in vacuo left methyl 5-fluorobenzofuran-3-carboxylate (125 g) as an oil.

The oil was dissolved in methanol (1.8 l) and magnesium turnings (7 g) was added.

After the reaction had started additional magnesium (80 g) was added portionswise during 1.5 h keeping the reaction temperature at 30–40° C. The reaction mixture was stirred for 1 h followed by addition of aq. ammonium chloride. Extraction with ether drying the ether phase over sodium sulfate followed by removal of the solvent in vacua, left a viscous oil, methyl 2,3-dihydro-5-fluorobenzofuran-3-carboxylate (120 g).

The oil was dissolved in 500 ml of dry ether and added dropwise to a suspension of lithium aluminium hydride (32 g) in 600 ml of dry ether. The mixture was refluxed for 3 h followed by hydrolysis with water. Filtration and removal of solvent in vacuo gave 2,3-dihydro-5-fluoro-3-hydroxymethyl-benzofuran (95 g) which was converted to 155 g of 2,3-dihydro-5-fluorobenzofuran-3-ylmethyl methanesulfonate by the method described in EXAMPLE 2.

Dimethyl malonate (262 g) was dissolved in NMP (2 l) and potassium tert-butoxide (202 g) was added portionwise keeping the temperature at 15–20° C. The mixture was heated to 60° C. and a solution of 2,3-dihydro-5-fluorobenzofuran-3-ylmethyl methanesulfonate (155 g) in NMP (150 ml) was added dropwise. The mixture was stirred for 4 h at 70–75° C. followed by addition of cold water. Extraction with ether, drying the ether phase over magnesium sulfate, followed by removal of solvent in vacuo gave dimethyl 2-(2,3-dihydro-5-fluorobenzofuran-3-ylmethyl) malonate (160 g) as an oil, which was sufficiently pure for the further synthesis.

The oil was dissolved in 2 l of ethanol and a mixture of 120 g of solid potassium hydroxide and 200 ml of water was added followed by reflux for 2 h. The reaction mixture was concentrated in vacuo, water was added followed by extraction with ether. The water phase was acidified with concentrated hydrochloric acid and extracted with ethyl acetate. Drying of the organic phase over magnesium sulfate and removal of solvent in vacua gave a viscous oil which was dissolved in NMP (1 l) and kept at 150° C. for 2 h. Addition of water and extraction with ether gave, after drying over magnesium sulfate and removal of solvent in vacuo, 77 g of 3-(2,3-dihydro-5-fluorobenzofuran-3-yl)-propionic acid. Reduction with lithium aluminium hydride by the method described above yielded 51 g of 3-(2,3-dihydro-5-fluorobenzofuran-3-yl)-1-propanol which was converted to 3-(2,3-dihydro-5-fluoro-benzofuran-3-yl)-1-propyl methanesulfonate by the method described in EXAMPLE 2.

The title compound, 11a, was prepared from 3-(2,3-dihydro-5-fluoro-benzofuran-3-yl)-1-propyl methanesulfonate (4.2 g) and 4-(4-fluorophenyl)piperidine (5.5 g) by the method described in EXAMPLE 2. Yield: 1.8 g, mp: 83–85° C.

In a similar manner was also prepared:
1'-[3-(2,3-Dihydro-5-fluoro-benzofuran-3-yl)-1-butyl]-spiro[isobenzofuran-1(3H),4'-piperidine], 11b, mp: 62–63° C.

EXAMPLE 12

1'-(4-(2,3-Dihydro-5-fluoro-benzofuran-3-yl)-1-butyl]-spiro[isobenzofuran-1(3H),4'-piperidine], oxalate, 12.

3-(2,3-Dihydro-5-fluoro-benzofuran-3-yl)-1-propanol, prepared as described in EXAMPLE 11, (51 g) was dissolved in 300 ml of dichloromethane and 0.5 ml of dimethyl formamide was added. During 20 min 50 ml of thionyl chloride was added dropwise followed by stirring for 3 h. Ice cold water was added, the organic phase separated, dried over magnesium sulfate and concentrated in vacuo giving 46 g of 3-(3-chloro-1-propyl)-2,3-dihydro-5-fluoro-benzofuran as an oil. Sodium cyanide (12 g) was suspended in dimethyl sulfoxide (180 ml) and heated to 80° C. A solution of 3-(3-chloro-1-propyl)-2,3-dihydro-5-fluoro-benzofuran (42 g) in 40 ml of dimethyl sulfoxide was added dropwise followed by heating to 140° C. for 15 min. After cooling ether and water were added, the ether phase separated, washed with water and dried over magnesium sulfate. Removal of solvent in vacuo left a viscous oil which was applied to a silica gel column giving 4-(2,3-dihydro-5-fluoro-benzofuran-3-yl)butyronitrile as an oil (20 g).

The cyanide was dissolved in 100 ml of glacial acetic acid followed by addition of concentrated hydrochloric acid (200 ml). After reflux for 5 h, water was added followed by extraction with ethyl acetate. Drying of the organic phase over magnesium sulfate and removal of solvent in vacuo gave 4-(2,3-dihydro-5-fluorobenzofuran-3-yl)butyric acid (20 g).

The acid (8 g) was dissolved in 50 ml of dichloromethane and 0.5 ml of dimethyl formamide was added. Thionyl chloride (20 ml) was added followed by reflux for 1.5 h. The reaction mixture was concentrated twice with heptane in vacuo giving 4-( 2,3-dihydro-5-fluoro-benzofuran-3-yl)-butyric acid chloride (7 9) as an oil.

A solution of spiro[isobenzofuran-1(3H),4'-piperidine] (2 g) and triethyl amine (3 ml) in dichloromethane (50 ml) was cooled to 5° C. and a solution of 4-(2,3-dihydro-5-fluoro-benzofuran-3-yl)-butyrlic acid chloride (3 g) in dichloromethane (25 ml) was added dropwise. After stirring for 1 h at room temperature the reaction mixture was washed with salt water and dried over magnesium sulfate. Removal of the solvent in vacua gave 4.4 g of a viscous oil which was dissolved in 25 ml of dry tetrahydrofuran and added dropwise to a suspension of lithium aluminium hydride (2.6 g) in 60 ml of dry tetrahydrofuran. The reaction mixture was heated to reflux for 2,h and hydrolyzed with water. Filtration and removal of solvent in vacuo gave a viscous oil which was applied to a silica gel column (eluent: heptane/ethyl acetate/triethyl amine=70:25:5) giving 2.9 g of the title compound, 12, which crystallized as the oxalate salt from acetone by addition of oxalic acid. Yield: 2.2 g, mp: 102–3° C.

EXAMPLE 13

1'-[4-(2,3-Dihydro-3-indolyl)-1-butyl]spiro[1,3-benzodioxole-2,4'-piperidine], oxalate,13a.

To a solution of 25b ( 4 g) and BH₃-NMe₃ (10 g) in 100 ml of dioxane, conc. hydrochloric acid (12 ml) was added.

After stirring for 0.5 h the mixture was refluxed for 2 h. The mixture was cooled to room temperature and 6 N hydrochloric acid (40 ml) was added followed by reflux for 1 h. The reaction mixture was made alkaline with aq. sodium hydroxide and extracted with dichloromethane. Drying of the organic phase over magnesium sulfate and removal of the solvent in vacuo gave an orange oil which was applied to a silica gel column (eluent: ethyl acetate/heptane/triethyl amine=70:28:2). The title compound, 13a, crystallized as the oxalate salt from acetone by addition of oxalic acid. Yield: 2.3 g, mp: 182–84° C.

In a similar manner were also prepared:
1'-[4-(2,3-Dihydro-3-indolyl)-1-butyl]spiro[isobenzofuran-1(3H),4'-piperidine], oxalate, 13b, mp: 161–64° C.
1'-[4-(2,3-Dihydro-3-indolyl)-1-butyl]spiro[1H-2-benzopyran-4(3H), 4'-piperidine],oxalate. 13c, mp: 105–7° C.
2,3-Dihydro-3-[4-(4-(2-methoxyphenyl)-1-piperidinyl)-1-butyl]indol, oxalate, 13d, mp: 160–62° C.

EXAMPLE 14

1'-[2-[5-Chloro-1-(4-fluorophenyl)-3-indolyloxy]-1-ethyl] spiro[isobenzofuran-1(3H) piperidine], oxalate, 14a.

To a solution of methyl 5-chloro-1-(4-fluorophenyl)-3-indolone-2-carboxylate (50 g) and potassium carbonate (40 g) in 500 ml of acetone, ethyl bromoacetate (35 g) in 100 ml of acetone was added dropwise under reflux. After reflux for 6 h the mixture was filtered and the solvent removed in vacuo. Addition of water and extraction with ether gave, after drying over magnesium sulfate and removal of solvent in vacua, a viscous oil, methyl 5-chloro-3-ethoxycarbonylmethoxy-1-(4-fluorophenyl)indole-2-carboxylate, 69g.

The oil was dissolved in 800 ml of ethanol and 30 g of potassium hydroxide added. Reflux for 4 h, addition of 4 1 of crushed ice followed by acidification with hydrochloric acid gave a colorless solid which was dissolved in 250 ml of NMP. Copper bronze (5 g) was added and the mixture kept at 200° C. for 4 h. Addition of water and extraction with ethyl acetate gave, after drying over magnesium sulfate and removal of solvent in vacua, 27 g of 5-chloro-1-(4-fluorophenyl)-3-indolyloxy acetic acid.

The acid was dissolved in 500 ml of tetrahydrofuran and lithium aluminium hydride (4 g) was added. After reflux for 3 h, the reaction mixture was hydrolyzed with Water, filtered, and concentrated in vacuo giving 18 g of 5-chloro-1-(4-fluorophenyl)-3-(2-hydroxyethyloxy)-indole as an oil.

The oil was dissolved in 250 ml of dichloromethane and triethyl amine (10 ml) was added. Methanesulfonyl chloride (10 ml) was added dropwise at 0–5° C. followed by stirring for 4 h. The reaction mixture was washed with water, dried over magnesium sulfate and concentrated in vacua, leaving 5-chloro-1-(4-fluorophenyl)-3-indolyloxyethyl methanesulfonate (21 g) as a viscous oil.

1-[2-[5-Chloro-1-(4-fluorophenyl)-3-indolyloxy]-1-ethyl]spiro[isobenzofuran-1(3H),4'-piperidine], 14a, was prepared from 5-chloro-1-(4-fluorophenyl)-3-indolyloxyethyl methanesulfonate (3 g) and spiro [isobenzofuran-1(3H),4'-piperidine] by the method described in EXAMPLE 2 followed by purification by column chromatography (silica gel, eluent: ethyl acetate). The title compound crystallized as the oxalate salt from acetone. Yield: 0.8 g, mp: 216–17° C.

In a similar manner was also prepared:
5-Chloro-1-(4-fluorophenyl)-3-f2-(4-(4-fluorophenyl)-1-piperidinyl)-1-ethyloxy]indol, 14b. mp: 102–5° C.

EXAMPLE 15

1'-[3-(5-Fluorobenzofuran-3-yl)-1-propyl)spiro [isobenzofuran-1(3H), 4'-piperidine], oxalate, 15.

The title compound was-prepared from 3-(5-fluorobenzofuran-3-yl) propionic acid (3 g) and spiro (isobenzofuran-1(3H),4'-piperidine] (2 g) by the method described in EXAMPLE 12. 3-(5-Fluoro-benzofuran-3-yl)-propionic acid was prepared by a procedure similar to the preparation of 3-(2,3-dihydro-5-fluorobenzofuran-3-yl)-propionic acid as described in EXAMPLE 11, but omitting the reduction with magnesium turnings. The title compound, 8, crystallized as the oxalate salt from acetone by addition of oxalic acid. Yield: 2.6 g, mp: 157–59° C.

EXAMPLE 16

1'-[4-(5-Fluorobenzofuran-3-yl)-1-butyl]-spiro [isobenzofuran-1(3H), 4'-piperidine],oxalate, 16.

The title compound was prepared from 4-(5-fluorobenzofuran-3-yl) butyric acid (3.5 g) and spiro [isobenzofuran-1(3H),4'-piperidine] (3 g) by the method described in EXAMPLE 12. 4-(5-Fluoro-benzofuran-3-yl) butyric acid was prepared by a procedure analogous to the preparation of 4-(2,3-dihydro-5-fluoro-benzofuran-3-yl) butyric acid as described in EXAMPLE 12, applying 3-(5-fluorobenzofuran-3-yl)-1-propanol instead of the corresponding dihydro analogue. 3-(5-Fluoro-benzofuran-3-yl)-1-propanol is prepared by the procedure described in EXAMPLE 11, but omitting the reduction with magnesium turnings. The title compound, 16 crystallized as the oxalate salt from acetone by addition of oxalic acid. Yield: 4.8 g. mp: 154–56° C.

EXAMPLE 17

1'-[4-[1-(4-Fluorophenyl)-5-trifluoromethylindazol-3-yl]-1-butyl]spiro[isobenzofuran-1(3H),4'-piperidine], 17a.

To a suspension of magnesium turnings (135 g) in 300 ml of dry tetrahydrofuran, ethyl bromide (140 g) dissolved in 500 ml of dry tetrahydrofuran was slowly added followed by reflux for 20 min. A solution of 4-chloro-1-butanol (274 g) in 500 ml of tetrahydrofuran was added dropwise at reflux temperature. After stirring for 20 min, the Grignard solution was filtered and added portionwise to a solution of 2-chloro-4-trifluoromethyl-benzonitrile (200 g) in 600 ml of dry tetrahydrofuran. The reaction mixture was stirred for 16 h at room temperature followed by addition af 2 N hydrochloric acid and ice. Extraction with ether drying of the ether phase over magnesium sulfate and removal of solvent in vacuo left a viscous oil which was applied to a silica gel column (eluent: dichloromethane/ether=3:1) giving 4-(2-chloro-5-trifluoromethylbenzoyl)-1-butanol (101 g) as an oil.

The oil (80 g) was dissolved in 800 ml of ethanol and hydrazine hydrate (160 ml) was added followed by refluxing for 20 h. The reaction mixture was cooled and concentrated in vacuo. Water was added followed by extraction with ether. Drying of the ether phase over magnesium sulfate and removal of solvent in vacua gave 79 g of the hydrazone of 4-(2-chloro-5-trifluoromethyl-benzoyl)-1-butanol as an oil. The hydrazone (20 g) was dissolved in dimethyl formamide and potassium tert-butoxide (10 g) was added. The mixture was kept at 100–120° C. for 30 min followed by addition of aq. ammonium chloride. Extraction with ethyl acetate, drying of the ethyl acetate phase over magesium sulfate, and removal of solvent in vacuo gave a viscous oil which was applied to a silica gel column (eluent: ethyl acetate) giving crystalline 4-(5-trifluoromethyl-3-indazolyl)-1-butanol (2.7 g, mp: 177–79° C.). The indazole (2.7 g) was arylated with 1-fluoro-4-iodobenzene (5 g) by the method described in EXAMPLE 5 giving 4-[1-(4-fluorophenyl)-5-trifluoromethyl-3-indazolyl]-1-butanol (2.7 g. mp: 77–79° C.) which was converted to the corresponding methanesulfonate by the method described in EXAMPLE 2. The title compound 7a, was prepared from the methanesulfonate (2 g) and spiro[isobenzofuran-1(3H ),4'-piperidine] (2 g) by the method described in EXAMPLE 2. Yield: 1.7 g, mp: 74–76° C.

In a similar manner was also prepared:
4-Fluorophenyl-3-[4-(4-(4-fluorophenyl)-1-piperidinyl)-1-butyl]-5-trifluoromethylindazol, 17b, mp: 124–25° C.

EXAMPLE 18

1'-[4-(5-Trifluoromethylindazol-3-yl)-1-butyl]-spiro [isobenzofuran-1(3H),4'-piperidine], 18.

4-(2-Chloro-5-trifluoromethylbenzoyl)-1-butanol, prepared as described in EXAMPLE 17, was converted to the corresponding methanesulfonate by the method described in EXAMPLE 2. Treatment with spiro[isobenzofuran-1(3H), 4'-piperidine] according to the method described in EXAMPLE 2 gave 1'-[4-(2-chloro-5-trifluoromethylbenzoyl)-1-butyl]-spiro[isobenzofuran-1 (3H),4'-piperidine]. Conversion to the corresponding hydrazone and ring closure according to the method described in EXAMPLE 17 gave the title compound, 18, mp: 146–47° C.

EXAMPLE 19

1'-(4-(1,2-Benzisoxazol-3-yl)-1-butyl)spiro[isobenzofuran-1(3H), 4'-piperidine], oxalate, 19a, mp: 164–65° C.

A solution of 1,2-benzisoxazole-3-acetic acid (prepared according to G. Casini et al, *J. Het. Chem.* 6, 1969, 279) (18 g), ether saturated with dry HCl (150 ml) and methanol (200 ml) was stirred for 2 h at room temperature. Removal of the volatiles in vacuo gave methyl 1,2-benzisoxazole-3-acetate (17 g) as an oil. The oil was dissolved in tetrahydrofuran (100 ml) and added dropwise to a suspension of lithium aluminium hydride (6 g) in tetrahydrofuran (200 ml) at 0–10° C. followed by stirring for 30 min at 15° C. Usual work-up gave 2-(1,2-benzisoxazol-3-yl)ethanol (13 g) as an oil.

The ethanol derivative (13 g) was converted to the corresponding methanesulfonate by the method described in EXAMPLE 2 (yield: 20 g). A solution of the methanesulfonate (20 g) in dimethyl sulfoxide (20 ml) was added to a suspension of sodium cyanide (15 g) in dimethyl sulfoxide (40 ml) at 70° C. followed by stirring for 30 min at 70–80° C. Water and ether was added the phases separated and the ether phase dried over magnesium sulfate. Removal of solvent in vacuo gave 3-(1,2-benzisoxazol-3-yl)propionitrile a solid (13 g, mp: 67° C.).

The nitrile was dissolved in methanol (200 ml) and HCl-saturated ether (200 ml) is was added followed by stirring for 16 h at room temperature. The reaction mixture was concentrated in vacuo, water and ether added and the phases separated. Drying of the ether phase over magnesium sulfate and removal of solvent in vacuo gave methyl 3-(1, 2-benzisoxazol-3-yl)propionate (13 g) as an oil.

By repeating the above mentioned steps the 3-(1,2-benzisoxazol-3-yl)propionate was converted to methyl 4-(1, 2-benzisoxazol-3-yl)butyrate which was reduced with lithium aluminium hydride according to the procedure described above to 4-(1,2-benzisoxazol-3-yl)-1-butanol. By the method described in EXAMPLE 2, 4-(1,2-benzisoxazol-3-yl)-1-butyl methanesulfonate was obtained.

The title compound 19a was obtained from 4-(1.2-benzisoxazol-3-yl)-1-butyl methanesulfonate (3.4 g) and spiro[isobenzofuran-1(3H),4'-piperidine] (2 g) by the procedure described in EXAMPLE 2. The oxalate salt crystallized from acetone by addition of oxalic acid. Yield: 2.4 g. mp: 164–65° C.

In a similar manner were also prepared:

3-[4-(4-(4-Fluorophenyl)-1-piperidyl)-1-butyl]-1,2-benzisoxazole, oxalate, 19b, mp:174–75° C.

1-(4-(1,2-Benzisoxazol-3-yl)-1-butyl)spiro[3H-2-benzopyran-3,4'-piperidine], oxalate, 19c, mp: 162–63° C.

3-[4-(4-(2,6-Dichlorophenyl)-1-piperidyl)-1-butyl]-1,2-benzisoxazol, fumarate, 19d, mp: 196–97° C.

EXAMPLE 20

1'-(3-(1,2-Benzisoxazol-3-yl)-1-propyl)spiro[isobenzofuran-1(3H), 4'-piperidine], oxalate, 20, mp: 131–32° C.

The title compound 20 was prepared from 3-(1,2-benzisoxazol-3-yl)-1-propan] (3.2 g, prepared as described in EXAMPLE 19 and spiro[isobenzofuran-1(3H),4'-piperidine] (2 g) by the method described in EXAMPLE 2. The product crystallized as the oxalate salt from acetone by addition of oxalic acid. Yield: 2.3 g, mp: 131–32° C.

EXAMPLE 21

3-[3-(4-(4-Fluorophenyl)-piperidin-1-yl)-1-propyloxy]-1,2-benzisothiazole, 21.

A mixture of 4-(4-fluorophenyl)-piperidine (15 g), ethyl 3-bromopropionate (20 g), and potassium carbonate (14 g) in methyl isobutyl ketone was refluxed for 16 h. Filtration and removal of solvent in vacuo gave 26 g of crude ethyl 3-(4-(4-fluorophenyl)-1-piperidyl)propionate as an oil which was used directly in the next step.

The oil was dissolved in dry tetrahydrofuran (70 ml) and added dropwise to a suspension of lithium aluminium hydride (6.5 g) in dry tetrahydrofuran (250 ml) at 15° C. under nitrogen gas. After stirring for 30 min at room temperature, water (6.5 ml), 10 N sodium hydroxide (7 ml), and water (30 ml) were added, subsequently. Filtration and removal of solvent gave 20 9 of crude 3-(4-(4-fluorophenyl)-1-piperidyl)-1-propanol as an oil which was sufficiently pure for use in the next step. A solution of 3-(4-(4-fluorophenyl)-1-piperidyl)-1-propanol (10 g) in dry toluene (150 ml) was treated portionwise with a 50% xylene suspension of sodium hydride (3 g). A solution of 3-chloro-1,2-benzisothiazole (3.6 g) in dry toluene (30 ml) was added dropwise at room temperature followed by stirring for 1.5 h at room temperature. Ice was added, the phases separated and the aqueous phase extracted with ether. Drying of the combined organic phases over magnesium sulfate and removal of solvents in vacuo gave an oil which was applied to column chromatography (silica gel, eluent: ethyl acetate/heptane/triethyl amine=50:50:4). The title compound 21 crystallized from a mixture of isopropyl ether/heptane. Yield:1.5 g, mp: 91–92–1C.

EXAMPLE 22

1'-(4-(1,2-Benzisothiazol-3-yl)-1-butyl)spiro[isobenzofuran-1(3H),4'-piperidine], oxalate, 22.

4-(1,2-Benzisothiazol-3-yl)butyric acid (C. Branca et al, *Phytochemistry* 14, 1975, 2545) (17 g) was dissolved in dry toluene (500 ml) and cooled to –10° C. Di-tert-butyl aluminium hydride (120 ml of an 1 M solution in toluene) was added dropwise at –10° C. followed by stirring for 2 h at room temperature. Dilute sulfuric acid (2 M, 300 ml) was added, the phases separated, the aqueous phase extracted with ether, and the combined organic phases dried over magnesium sulfate. Removal of solvents in vacuo left a viscous oil which was purified by column chromatography (silica gel, eluent: ether). 4-(1,2-Benzisothiazol-3-yl)-1-butanol (5.2 g) was obtained as an oil.

The title compound 22 was obtained from 4-(1,2-benzisothiazol-3-yl)-1-butanol and spiro[isobenzofuran-1(3h),4'-piperidine] by the method described in EXAMPLE 2. The oxalate salt crystallized from acetone by addition of oxalic acid. Yield: 2 g, mp: 151–52° C.

EXAMPLE 23

1-(4-Fluorophenyl)-3-[4-[3-(4-fluorophenyl)-8-azabicyclo[3,2,1]-oct-2-en-8-yl]-1-butyl]-indol, 23.

A mixture of dry ether (600 ml) and 15% BuLi in hexane (500 ml) was cooled to –45° C. A solution of 4-bromo-1-fluorobenzene (145 g) in dry ether (350 ml) was added dropwise at –45° C. followed by stirring for 1 h. A solution of 8-methyl-8-azabicyclo[3.2.1]octan-3-one (85 g) in dry ether (400 ml) was added dropwise at –50° C. followed by stirring for 30 min. the temperature raising to –20° C. The reaction mixture was poured into 2 M hydrochloric acid and the phases separated.

The ether phase was extracted with 2 M hydrochloric acid and the combined aqueous phases made alkaline with aqueous NaOH. Extraction with ethyl acetate drying of the organic phase over magnesium sulfate and removal of solvent in vacuo, gave 3-(4-fluorophenyl)-3-hydroxy-8-methyl-8-azabicyclo(3,2,1 ]octane (96 g) as a solid, mp: 169° C.

The product was dissolved in trifluoroacetic acid (500 ml) followed by reflux for 1 h. The reaction mixture was concentrated in vacuo, water added and the mixture made alkaline with aqueous NaOH (pH>9). Extraction with ethyl acetate, drying of the organic phase over magnesium sulfate, and removal of solvent in vacuo gave 3-(4-fluorophenyl)-8-methyl-8-azabicyclo[3,2,1]oct-2-ene as a solid (91 g, mp: 62–63° C).

The product was dissolved in 1,1,1-trichloroethane (550 ml) and heated to 70° C. A solution of 2.2.2-trichloroethyl chloroformate (14 ml) in 1,1,1-trichloroethane (25 ml) was added dropwise at 70° C. followed by reflux for 1 h. Additional 2.2.2-trichloroethyl chloroformate (24 ml) was added followed by reflux for 5 h. Removal of volatiles in vacuo and-purification by column chromatography (silica gel, eluent: methylene chloride) gave 3-(4-fluorophenyl)-8-(2,2,2-trichloroethyloxycarbonyl)-8-azabicyclo[3,2,1]oct-2-ene (59 g) as an oil.

(4-Fluorophenyl)-8-(2,2,2-trichloroethyloxycarbonyl)-8-azabicyclo[3,2,1 ]oct-2-ene (17 g) was dissolved in glacial acetic acid (170 ml) followed by addition of water (20 ml). The mixture was heated to 50° C. and zink dust (40 g) was added in portions. After stirring for 2 h at 50° C. the mixture was filtered and concentrated in vacuo. Water was added and the mixture made alkaline with aqueous NaOH.

Extraction with ethyl acetate, drying of the organic phase over magnesium sulfate and removal of solvent in vacuo left 3-(4-fluorophenyl)-8-azabicyclo[3,2,1]oct-2-ene (7 g) as an oil.

The title compound 23 was prepared from 3-(4-fluorophenyl)-8-azabicyclo[3,2,1]oct-2-ene according to the method described in EXAMPLE 9. Yield: 1.9 g, mp: 74–75°

C.

EXAMPLE 24

3-[4-[3-(4-Fluorophenyl)-8-azabicyclo[3.2. 1 octan-8-yl]-1-butyl]-1,2-benzisoxazole,oxalate, 24, mp 169–170.

A solution of 3-(4-fluorophenyl)-8-azabicyclo[3,2,1]oct-2-ene (10 g) was dissolved in glacial acetic acid (150 ml). Platinum oxide (0.5 g) was added followed by treatment with hydrogen gas at 3 atm of pressure in a conventional Parr apparatus.

Filtration and removal of solvent in vacuo left a viscous oil. Water was added and the mixture made alkaline (pH>9) with aqeous NaOH. Extraction with ethyl acetate, drying of the organic phase over magnesium sulfate and removal of solvent in vacuo gave 3-(4-fluorophenyl)-8-azabicyclo[3,2,1]-octane (9 g) as an oil.

The title compound 24 was obtained from 3-(4-fluorophenyl)-8-azabicyclo[3.2.1 ]octane and 4-(1.2-benzisoxazol-3-yl)-1-butyl methanesulfonate (prepared as described in EXAMPLE 19) by the method described in EXAMPLE 2. The oxalate salt crystallized from acetone by addition of oxalic acid. Yield. 1.1 g, mp: 169–70° C.

EXAMPLE 25

1'-(4-Phenyl-1-butyl)-spiro[1,3-benzodioxole-2,4'-piperidine], maleate, 25a.

A mixture of 1-ethoxycarbonyl-4-piperidinone (17 g), pyrocatechol (13 g) and p-toluenesulfonic acid (2.5 g) in 250 ml of dry toluene was refluxed with continous removal of water. After 3 h the reaction mixture was concentrated in vacua, 2% NaOH (200 ml) was added followed by extraction with dichloromethane. After drying over magnesium sulfate and removal of solvent in vacuo, the remaining red oil was applied to a silica gel column (eluent: ethyl acetate/heptane =1:1) giving 22 g of a slightly yellow oil, 1'-ethoxycarbonyl-spiro[1,3-benzodioxole-2,4'-piperidine].

The oil was dissolved in ethanol (250 ml), NaOH (10 g) and water (20 ml) were added and the mixture refluxed for 20 h. Removal of the solvents in vacuo addition of salt water followed by extraction with dichloromethane gave, after drying the organic phase over magnesium sulfate and removal of the solvent in vacuo, a red oil which was applied to a silica gel column (eluent: ethyl acetate/methanol/triethylamine=4:5:1) yielding 10 g of colorless crystals, spiro[1,3-benzodioxole-2,4'-piperidine], mp: 108–10° C.

The title compound, 25a, prepared from 4-phenyl.-1-butyl methanesulfonate (2.3 g) and spiro[1,3-benzodioxole-2,4'-piperidine] (1.9 g) according to the method described in EXAMPLE 2, crystallized as the maleate salt from acetone by addition of maleic acid. Yield: 1.6 g. mp: 156–57° C.

In a similar manner was also prepared: 1'-[4-(3-Indolyl)-1-butyl]-spiro[1.3-benzodioxole-2,4'-piperidine], 25b, mp: 144–49° C.

EXAMPLE 26

1'-[4-(4-Fluorophenyl)-4-hydroxy-1-butyl]-spiro[isobenzofuran-1(3H),4'-piperidine],oxalate, 26a.

1'-(3-(4-Fluorobenzoyl)-t-propyl)-spiro[isobenzofuran-1(3h),4'-piperidine], oxalate (2 g), obtained from 1-chloro-3-(4-fluorobenzoyl)-propane and spiro[isobenzofuran-1(3H), 4'-piperidine] by the method described in EXAMPLE 1, was dissolved in 100 ml of EtOH. Platinum oxide (0.1 g) was added and the mixture was hydrogenated in a Parr apparatus at 3 atm of hydrogen pressure for 16 h. Filtration and concentration in vacuo gave after addition of a mixture of ethyl acetate/acetone, crystalline 26a. Yield: 1.5 g. mp: 75–80° C.

In a similar manner were also prepared:
1'-(4-Phenyl-4-hydroxy-1-butyl)-spiro[isobenzofuran-1(3H),4'-piperidine], 26b, mp: 139–40° C.
1'-(4-Cyclohexyl-4-hydroxy-1-butyl)spiro[isobenzofuran-1(3h),4'-piperidine], oxalate, 26c, mp: 87–89° C.

EXAMPLE 27

1'-(4-(1H-Inden-3-yl)-1-butyl)-spiro[isobenzofuran-1(3H),4'-piperidine], 27.

A suspension of activated zinc (80 g) in dry tetrahydrofuran (200 ml) was heated to reflux and a few crystals of iodine was added. A solution of 1-indanone (100 g) and methyl 4-bromo-crotonate (200 g) in 500 ml of dry tetrahydrofuran was added dropwise followed by reflux for 1 h. After cooling, ice and aq. ammonium chloride was added followed by extraction with dichloromethane. Removal of the solvent in vacuo gave a viscous oil which was purified on a silica gel column (eluent: dichloromethane/ether =1:1) giving methyl 4-(1-hydroxyindan-1-yl)-crotonate (78 g). A solution of the crotonate (20 g) was dissolved in 200 ml dry ether and added dropwise to a suspension of lithium aluminium hydride (10 g) in 150 ml of dry ether. After reflux for 1 h, the reaction mixture was hydrolyzed with water. Filtration, drying of the ether phase over magnesium sulfate, and removal of solvent in vacuo gave 4-(1-hydroxyindan-1-yl)-1-butanol (18 g) as an oil. The alcohol (16 g) was dissolved in methanol (250 ml) and concentrated hydrochloric acid (40 ml) was added. After stirring for 30 min at room temperature, the reaction mixture was concentrated in vacua. water was added and the mixture extracted with ether. Drying of the ether phase over magnesium sulfate and removal of solvent in vacuo gave a viscous oil which was applied to a silica gel column (eluent: dichloromethane/ether=9:1) giving 4-((1H)inden-3-yl)-1-butanol (1.8 g)

By the method described in EXAMPLE 2, the alcohol was converted to the corresponding methanesulfonate and the title compound, 27, was obtained using spiro[isobenzofuran-1(3H),4'-piperidine), mp: 79–80° C.

EXAMPLE 28

1'-[4-(Indan-1-yl)-1-butyl]-spiro(isobenzofuran-1(3H),4'-piperidine], oxalate, 28.

A suspension of activated zinc (40 g) in dry tetrahydrofuran (150 ml) was heated to reflux and a few crystals of iodine was added. A solution of 1-indanone (50 g) and methyl 4-bromo-crotonate (100 g) in 400 ml of dry tetrahydrofuran was added dropwise followed by reflux for 1 h. After cooling, ice was added and the pH adjusted to 1 with concentrated hydrochloric acid followed by extraction with dichloromethane. Concentration of the organic phase left a viscous oil which was dissolved in methanol (400 mn). Concentrated hydrochloric acid.(100 ml) was added and the mixture stirred for 30 min. Removal of solvents in vacua, addition of water, and extraction with ether gave, after drying over magnesium sulfate and removal of solvent in vacuo, an oil (34 g). The oil was dissolved in 300 ml of dry ether and added dropwise to a suspension of lithium aluminium hydride (21 g). After reflux for 2 h, the reaction mixture was hydrolyzed with water. Filtration and removal of solvent in vacuo gave a mixture of isomers from which 4-(1-indanyl)-but-3-en-1-ol (6 g) could be isolated by column chromatography (silica gel, eluent: dichloromethane] ether=9:1). The remaining mixture of isomers (9 g) was dissolved in 150 ml of methanol and hydrogenated at 3 atm of hydrogen pressure in a conventional Parr apparatus in the presence of 5% palladium on charcoal (6 g) for 12 h.

Filtration and removal of solvent in vacua gave 6 g of 4-(1-indanyl)-1-butanol.

The alcohol was converted to the title compound, 28, via the corresponding methanesulfonate following the procedures described in EXAMPLE 2 using spiro[isobenzofuran-1(3H),4'-piperidine], mp: 114–15° C.

EXAMPLE 29

1'-[4-(1-Indanyl)-but-3-en-1-yl]-spiro[isobenzofuran-1 (3H),4'-piperidine], oxalate, 29.

4-(1-Indanyl)-but-3-en-1-ol, prepared as described in EXAMPLE 28, was converted to the corresponding methanesulfonate by the method described in EXAMPLE 2.

The title compound was prepared by the method described in EXAMPLE 2 using spiro[isobenzofuran-1(3H),4'-piperidine], mp: 108–9° C.

EXAMPLE 30

1'-(4-(2,3-Dihydro-1-(4-fluorophenyl)-3-indolyl)-1-butyl) spiro[isobenzofuran-1(3H),4'-piperidine], oxalate, 30.

To a solution of 5a (2 g) in trifluoroacetic acid (30 ml), sodium cyanborohydride (0.5 g) in methanol (25 ml) was added dropwise. After stirring for 2 h at room temperature the mixture was concentrated in vacuo, ethyl acetate (50 ml) was added followed by washing with 2 N sodium hydroxide (2×50 ml). Drying of the organic phase over sodium sulfate and removal of solvent in vacuo gave the title base which crystallized as the oxalate salt from acetone by addition of oxalic acid. Yield: 0.7 g, mp: 172–73° C.

EXAMPLE 31

1'-[3-(Benzo[b]thiophen-3-ylthio)-1-propyl]spiro [isobenzofuran-1(3,4'-piperidine], maleate,31a.

A solution of benzo[b]thiophen-3-one (20 g), 3-mercaptopropionic acid (25 ml), 2 N hydrochloric acid (3 ml) in xylene (80 ml) was refluxed for 18 h. Water (100 ml) and ether (300 ml) were added and the phases separated. The ether phase was extracted with 150 ml 2 N NaOH followed by acidification of the alkaline phase with conc. hydrochloric acid. Extraction with ether, drying of the ether phase over magnesium sulfate and removal of solvent gave 15.6 g of a viscous oil, 3-(benzo[b]thiophen-3-ylthio)-propionic acid.

The acid was dissolved in 100 ml of tetrahydrofuran and added dropwise to a suspension of lithium aluminium hydride (4 g) in tetrahydrofuran (150 ml). After reflux for 3 h, the reaction was quenched with water followed by usual work-up giving 12.7 g of 3-(benzo[b]thiophen-3-ylthio)-1-propanol as an oil. The title compound 31a was obtained by the method described in EXAMPLE 2 using spiro [isobenzofuran-1(3H),4'-piperidine) and crystallized as the maleate from acetone by addition of maleic acid. Yield: 0.9 g. mp: 154–55° C.

In a similar manner was also prepared:

1'-[3-(Benzo[b]thiophen-3-ylthio)-1-propyl] spiro[3H-2-benzopyran-3,4'-piperidine]maleate, 31b, mp: 169–70° C.

EXAMPLE 32

1'-[4-(2.3-Dihydro-benzo[b]thiophen-3-yliden)-1-butyl] spiro[isobenzofuran-1(3H),4'-piperidine]-S,S-dioxide, maleate, 32.

A solution of 4-(3-benzo[b]thiophen-3-yl)-1-butyl methanesulfonate (4.4 g), prepared as described in EXAMPLES 10 and 2, in glacial acetic acid (12 ml) was treated dropwise with aqeous 30 % hydrogen peroxide at room temperature followed by heating to 80° C. for 20 min. Upon cooling the product, 4-(3-benzo[b]thiophen-S,S-dioxide-3-yl)-1-butyl methanesulfonate, crystallized. Yield: 3.7 g, mp: 100–1° C.

The methanesulfonate (1.4 g) was treated with spiro [isobenzofuran-1(3H),4'-piperidine]-HCl (1.2 g) according to the method described in EXAMPLE 2 giving the title compound 32 which crystallized as the maleate from acetone by addition of maleic acid. Yield: 1 g, mp: 186–87° C.

EXAMPLE 33

1'-[4-(2,3-Dihydro-benzo[b]thiophen-3-yl)-1-butyl]spiro [isobenzofuran-1(3H),4'-piperidine]-S,S-dioxide, maleate, 33.

Oxidation of 4-(benzo[b]thiophen-3-yl)butyric acid (8.5 g) according to the method described in EXAMPLE 32 gave the corresponding S,S-dioxide (9.2 g). A solution of the acid (4 g) in tetrahydrofuran (25 ml) was added dropwise to a suspension of lithium aluminium hydride (1.3 g) in tetrahydrofuran (50 ml) at 0° C. followed by stirring at room temperature for 2 h. Usual work-up yielded 3 g of 4-(2,3-dihydro-benzo[b]thiophen-S,S-dioxide-3-yl)-1-butanol which was converted to the title compound by treatment with spiro[isobenzofuran-1(3H),4'-piperidine]according to the method described in EXAMPLE 2. The product crystallized as the fumarate from an acetone/ethanol mixture upon addition of fumaric acid. Yield: 1.5 g, mp: 197–98° C.

EXAMPLE 34

1'-[3-(Benzo[b]thiophen-3-yloxy)-1-propyl]spiro [isobenzofuran-1(3H),4'-piperidine], maleate, 34.

A mixture of benzo[b]thiophen-3-one (30 g), ethyl 3-bromopropionate (73 g), potassium carbonate (55 g), potassium iodide (1.3 g) and acetone (600 ml) was refluxed for 18 h. Filtration and removal of solvent in vacuo a red oil which was dissolved in ether (200 ml) and dried over magnesium sulfate. The ether solution was added dropwise to a suspension of lithium aluminium hydride (5 g) in ether (100ml) followed by reflux for 1 h. Usual work-up gave a viscous oil which was applied to a silica gel column (eluent: isopropyl ether) giving 3-(benzo(b]thiophen-3-yloxy)-1-propanol (0.54 g) as an oil.

The title compound was obtained according to the method described in EXAMPLE 2 using spiro[isobenzofuran-1(3H), 4'-piperidine] and crystallized as the maleate salt from an acetone/ether mixture by addition of maleic acid. Yield: 0.34 g, mp: 116–17° C.

EXAMPLE 35

1'-[2-(Benzo[b]thiophen-3-ylmethyloxy)-1-ethyl]spiro [isobenzofuran-1(3H),4'-piperidine], fumarate, 35a.

An ether solution (50 ml) of methyl benzo[b]thiophene-3-carboxylate (15 g) was added dropwise to a suspension of lithium aluminium hydride (3.5 g) in ether (100 ml) followed by reflux for 2 h. Usual work-up gave benzo[b] thiophen-3-yl methanol (13.5 g) as an oil.

The oil was dissolved in tetrahydrofuran (50 ml) and added dropwise to a suspension of NaH (5 g of an 80% paraffinsuspension) in tetrahydrofuran (100 ml) followed by reflux for 1 h. Ethyl bromoacetate (35 g) in tetrahydrofuran (50 ml) was added at 60° C. followed by reflux for 1 h. Additional ethyl bromoacetate (20 g) was added followed by reflux for 7 h. The reaction was quenched with water and the volatiles removed in vacuo. The remaining oil was applied to a silica gel column (eluent: ethyl acetate/heptane 2:8) giving ethyl benzo[b]thiophen-3-ylmethyloxyacetate (5 g) as an oil. Reduction with lithium aluminium hydride as described above yielded 3.8 g of 2-(benzo[b]thiophen-3-ylmethyloxy)ethanol as an oil.

The title compound 35a was obtained by the method described in EXAMPLE 2 using spiro[isobenzofuran-1(3H), 4'-piperidine] and crystallized as the fumarate salt from an acetone/ethanol mixture by addition of fumaric acid. Yield: 0.55 g, mp: 149–50° C.

In a similar manner was also prepared:

1'-[2-(5-Fluorobenzofuran-3-ylmethyloxy)-1-ethyl]spiro [isobenzofuran-1(3H),4'-piperidine], oxalate, 35b, mp: 148–49° C.

1'-[2-(Benzofuran-3-ylmethyloxy)-1-ethyl]-4-fluorospiro [isobenzofuran-1(3H),4'-piperidine], oxalate, 35c, mp: 120–22° C.

EXAMPLE 36

1'-[4-(1-(2-Dimethylamino-1-ethyl)-3-indolyl)-1-butyl] spiro[isobenzofuran-1(3H), 4'-piperidine], dihydrochloride, 36.

A solution of 4-(3-indolyl)-1-butanol (5 g) in dry DMF (50 ml) was cooled to 10° C. followed by treatment with potassium t-butoxide (3 g). After stirring for 5 min. 2-chloro-N,N-dimethylacetamide (3.5 g) dissolved in dry DMF (10 ml) was added dropwise at 10–15° C. After stirring for 1 h at room temperature water was added followed by extraction with ethyl acetate. Drying of the organic phase over magnesium sulfate and removal of solvent in vacuo left a viscous oil, 4-(1-dimethylaminocarbonylmethyl-3-indolyl)-1-butanol (7 g) which was converted to 1'-[4-(1-dimethylaminocarbonylmethyl-3-indolyl)-1-butyl]spiro [isobenzofuran-1(3),4'-piperidine] by the method described in EXAMPLE 2 using spiro[isobenzofuran-1(3H),4'-piperidine]. Yield: 5.7 g of a viscous oil. Conventional reduction with lithium aluminium hydride gave the title compound 36 which crystallized as the dihydrochloride from acetone by addition of hydrochloric acid. Yield: 2.4 g, mp: 244–45° C.

PHARMACOLOGY

Some of the compounds of Formula I have been tested according to an established and reliable pharmacological test as follows:

INHIBITION OF 3H-DTG BINDING TO SIGMA RECEPTORS IN RAT BRAIN IN VITRO

By this method the inhibition by drugs of the binding of 2 nM $^3$H-DTG (1,3-di-o-tolyl guanidine) to sigma receptors in homogenates or membranes from rat brain without cerebellum is determined in vitro as modified from Weber et al. *Proc. Natl. Acad. Sci.* 1986, 83,8784.

Tissue preparations:

Homogenate: Rats (150–250 g) are decapitated and the brains (without cerebellum) quickly removed and placed on ice, weighed and homogenized in 100 vol ice-cold (0° C.) 50 mM Tris-buffer (pH 7.7) in an ethanol rinsed glass/teflon homogenizer at 0° C. and kept on ice until use.

P2-membranes: Brains are homogenized in 10 vol 0.32 M sucrose in an ethanol rinsed glass/teflon homogenizer with 10 strokes up and down. The homogenate is centrifuged for 10 min at 900×$g_m$ at 4° C. The supernatant is decanted and centrifuged for 20 min at 50,000 $g_m$ at 4° C. The resulting pellet is resuspended in 10 vol ice-cold 50 nM Tris-buffer (pH 7.7) and incubated for 30 min. at 37° C. The membrane suspension is then centrifuged for further 20 min. at 50,000 $g_m$ at 4° C. The pellet is resuspended in 50 vol. of ice-cold Tris-buffer and used immediately.

Binding analysis:

0.5 ml 50 mM Tris-buffer (pH 7.7), 0.25 ml displacer (6×100 µM DTG, 6× [test compound], or Tris-buffer), and 0.25 ml 6×2 nM. $^3$H-DTG are mixed into 5 ml s plastic test tubes and kept at 4° C. until use. The binding reaction is initiated by mixing 0.5 ml tissue suspension into this solution and incubate at 25° C. for 20 min. Glass fiber filters (Whatman GF/B) are placed on the filter machine which is then closed tightly. Just before filtration vacuum is applied, and the filters washed with 0.1% PEI solution from a spray bottle followed by one wash with Tris-buffer.

The binding reaction is stopped by filtration of the assay mixture at reduced pressure (750 mbar) followed by further 3 washes with 5 ml ice-cold Tris-buffer. The filters are then placed in counting vials and 4 ml scintillation solution added. The vials are counted in a Beckmann scintillation counter.

Buffers and solutions:

50 mM Tris-buffer pH 7.7: 7.38 g Trizma—7.7 plus distilled $H_2O$ ad 1 liter. 100 ml 10% polyethylenimine (PEI): 100 ml dest. $H_2O$ is added to approx. 20 g 50% PEI which is solubilized by stirring and heating. Diluted (1+99) before use. 6×2 nM $^3$H-DTG: The exact volume depends on the actual concentration of the batch, but is made as close as possible to 12 nM. The containers for the radioactive solution is rinsed in 96% ethanol before use.

6×100 µM DTG: 14.36 mg/100 ml is kept frozen in 10 ml aliqouts.

$^3$H-DTG was obtained from NEN Research Products, Du Pont Denmark. Specific activity 62.3 Ci/mmol.

The known sigma receptor ligands BMY 14802 and rimcazole were included in the test for comparison purposes.

TABLE 1

$^3$H DTG Binding Data

| Compound IC50 | (nM) | Compound IC50 | (nM) | Compound IC50 | (nM) |
|---|---|---|---|---|---|
| 1a | 7.3 | 4c | 2.9 | 11a | 0.31 |
| 1b | 3.7 | 4d | 1.1 | 11b | 0.63 |
| 2a | 0.25 | 4e | 0.20 | 12 | 0.30 |
| 2b | 0.07 | 4f | 0.20 | 13a | 3.7 |
| 2c | 0.51 | 4g | 46 | 13b | 1.0 |
| 2d | 0.77 | 5a | 0.33 | 13c | 4.8 |
| 2e | 1.2 | 5b | 1.1 | 13d | 2.1 |
| 2f | 0.95 | 5c | 0.25 | 14a | 24 |
| 2g | 0.36 | 5d | 0.24 | 14b | 3.8 |
| 2h | 1.4 | 5e | 4.7 | 15 | 0.42 |
| 2i | 4.3 | 5f | 0.04 | 16 | 0.15 |
| 2j | 0.07 | 5g | 4.0 | 17a | 0.11 |
| 2k | 0.19 | 6a | 0.05 | 17b | 0.46 |
| 2l | 3.8 | 6b | 0.17 | 18a | 0.56 |
| 2m | 0.47 | 6c | <0.1 | 19a | 0.08 |
| 2n | 6.0 | 7 | 0.21 | 19b | 0.49 |
| 2o | 0.26 | 8a | 0.21 | 19c | 0.84 |
| 2p | 0.32 | 8b | 1.7 | 19d | 4.4 |
| 2q | 430 | 8c | 0.66 | 20 | 0.63 |
| 2r | 3.0 | 8d | 11 | 21 | 0.2 |
| 2s | 3.1 | 9a | 0.34 | 22 | 0.05 |
| 2t | 5.4 | 9b | 0.06 | 23 | 2.5 |
| 2u | 0.41 | 9c | 0.14 | 24 | 1.9 |
| 2v | 1.8 | 9d | 26 | 25a | 11 |
| 2x | 1.6 | 9e | 0.31 | 25b | 36 |
| 2y | 0.84 | 9f | 27 | 26a | 0.89 |
| 2z | 1.5 | 9g | 4.2 | 26b | 1.9 |
| 2aa | 0.3 | 9h | 2.3 | 26c | 0.14 |
| 2bb | 0.30 | 9i | 0.62 | 27 | 0.11 |
| 2cc | 1.1 | 9j | 0.11 | 28 | 0.15 |
| 2dd | 1.7 | 9k | 0.92 | 29 | 0.12 |
| 2ee | 1.0 | 9l | 0.14 | 30 | 0.07 |

TABLE 1-continued $^3$H DTG Binding Data

| Compound | IC50 (nM) | Compound | IC50 (nM) | Compound | IC50 (nM) |
|---|---|---|---|---|---|
| 2ff | 0.43 | 9m | 1.6 | 31a | 0.23 |
| 2gg | 3.3 | 9n | 6.3 | 31b | 2.6 |
| 2hh | 0.02 | 9o | 6.7 | 32 | 0.89 |
| 2ii | 5.8 | 9p | 0.28 | 33 | 0.95 |
| 2jj | 1.4 | 9q | 0.12 | 34 | 0.27 |
| 3a | 2.2 | 9r | 0.42 | 35a | 0.73 |
| 3b | 4.8 | 9s | 56 | 35b | 2.8 |
| 3c | 1.0 | 9t | 3.2 | 36 | 4.5 |
| 3d | 7.3 | 10a | 0.09 | | |
| 4a | 23 | 10b | 1.3 | BMY 14802 | 230 |
| 4b | 0.53 | 10c | 0.35 | rimcazole | 180 |

It is seen from Table I that the compounds used in the present invention are very potent sigma receptor ligands as compared to the reference compounds which are known in the art to be sigma receptor ligands, the potencies for the compounds tested being better than about 40 nM, and for most of the compounds tested better than about 1 nm.

Furthermore, the ability of the present compounds in inhibiting the binding of $^3$H-Prazosin to a, adrenoceptors in membranes from rat brain were determined in vitro according to Hyttel, J et al, *J. Neurochem*, 1985, 44, 1615; Skarsfeldt, T. et al, *Eur. J. Pharmacol.* 1986, 125, 323.

Additionally the compounds of the invention were tested with respect to dopamine $D_2$ receptor binding activity according to van der Welde et al, *Eur. J. Pharmacol.* 1987, 134, 211.

For most compounds, the affinities for $\alpha_1$ adrenoceptors and $D_2$ receptors were weak as compared to the potent binding to sigma receptors. Thus many of the compounds are very selective sigma receptor ligands, having ratios of binding affinities ($IC_{50}$ alpha/$IC_{50}$ sigma and $IC_{50}$ dopamine/$IC_{50}$ sigma, respectively) of 30–10000.

LIGHT/DARK DISCRIMINATION TEST IN RATS

The test was carried out in accordance with F. C. Colpaert et al., Psychopharmacology (1985) 86: 45–54. The test used Wistar WU rats.

The test was conducted using a two compartment activity box in which the actions of anxiolytic compounds to reduce aversion against a brightly-lit environment may be readily detected. The box is designed as an open-top experimental box one third of which was partitioned from the rest, painted black and illuminated with red light. The remainder of the box was painted white and brightly illuminated. The floor of each area was lined into squares. Behavioural changes were recorded. Data obtained from dose groups were analysed using single factor analysis of variance, and Dunnett's t-test. Test compounds were given intraperitoneally 45 min before testing.

Several compounds have been tested in this test model and showed significant anxiolytic activities with $ED_{50}$ values in the ng-$\mu$g/kg dose range.

FORMULATION EXAMPLES

The pharmaceutical formulations of the invention may be prepared by conventional methods in the art.

For example: Tablets may be prepared by mixing the active ingredient with ordinary adjuvants and/or diluents and subsequently compressing the mixture in a conventional tabletting machine. Examples of adjuvants or diluents comprise: corn starch, potato starch, talcum, magnesium stearate, gelatine, lactose, gums, and the like. Any other adjuvants or additives usually used for such purposes such as colourings, flavourings, preservatives etc. may be used provided that they are compatible with the active ingredients.

Solutions for injections may be prepared by dissolving the active ingredient and possible additives in a part of the solvent for injection, preferably sterile water, adjusting the solution to desired volume, sterilization of the solution and filling in suitable ampules or vials. Any suitable additive conventionally used in the art may be added, such as tonicity agents, preservatives, antioxidants, etc.

Typical examples of recipes for the formulation of the invention are as follows:

1) Tablets containing 0.5 milligrams of Compound 3c calculated as the freebase:

| | |
|---|---|
| Comp. 3c | 0.5 mg |
| Lactose | 18 mg |
| Potato starch | 27 mg |
| Sucrose | 58 mg |
| Sorbitol | 3 mg |
| Talcum | 5 mg |
| Gelatine | 2 mg |
| Povidone | 1 mg |
| Magnesium stearate | 0.5 mg |

2) Tablets containing 5 milligrams of Compound 2m calculated as the free base:

| | |
|---|---|
| Comp. 2m | 5 mg |
| Lactose | 16 mg |
| Potato starch | 45 mg |
| Sucrose | 106 mg |
| Sorbitol | 6 mg |
| Talcum | 9 mg |
| Gelatine | 4 mg |
| Povidone | 3 mg |
| Magnesium stearate | 0.6 mg |

3) Syrup containing per milliliter:

| | |
|---|---|
| Comp. 6b | 2.5 mg |
| Sorbitol | 500 mg |
| Tragacanth | 7 mg |
| Glycerol | 50 mg |
| Methyl-paraben | 1 mg |
| Propyl-paraben | 0.1 mg |
| Ethanol | 0.005 ml |
| Water | ad 1 ml |

4) Solution for injection containing per milliliter:

| | |
|---|---|
| Comp. 17 a | 1 mg |
| Acetic acid | 17.9 mg |
| Sterile water | ad 1 ml |

5) Solution for injection containing per milliliter:

| | |
|---|---|
| Comp. 17b | 0.1 mg |
| Sorbitol | 42.9 mg |
| Acetic acid | 0.63 mg |
| Sodium hydroxide | 22 mg |
| Sterile water | ad 1 ml |

What is claimed is:

1. A method for treating anxiety, epilepsy, convulsion, movement disorder, or amnesia by action on sigma receptors, comprising adminisering to a patient in need thereof a therapeutically effective amount of a sigma receptor binding compound of formula I:

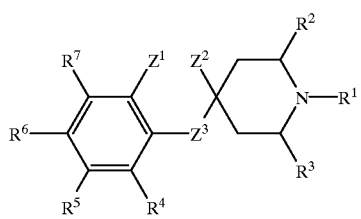

wherein $R^1$ is a group having the Formula II:

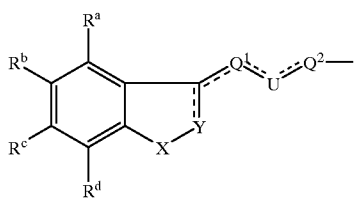

wherein X is $CHR^{10}$, O, S, SO, $SO$, or $NR^{10}$, $R^{10}$ being hydrogen, lower alkyl, lower alkenyl, cycloalkyl, cycloalkylalkyl, cycloalkenyl or cycloalkenylalkyl, acyl, aminoalkyl, mono- or dialkylaminoalkyl, sulfonyl or arylalkyl or phenyl optionally substituted with one or more substituents independently selected from the group consisting of halogen, lower alkyl, lower alkoxy, hydroxy, trifluoromethyl, and cyano, or $R^{10}$ is 2-thienyl, 3-thienyl, 2-furanyl, 3-furanyl, 2-thiazolyl, 2-oxazolyl, 2-imidazolyl, 2-pyridyl, 3-pyridyl, or 4-pyridyl;

one or two of the dashed lines may be a bond;

when he dotted line emanating from Y indicates a bond, Y is N or CH; or when said dotted line indicates no bond, Y is $CH_2$, NH, C=O or C=S;

$R^a$–$R^d$ is independently selected from the group consisting of hydrogen, halogen, lower alkyl, lower alkoxy, hydroxy, lower alkylthio, lower alkylsulphonyl, lower alkylamino, lower dialkylamino, cyano, trifluoromethyl, or trifluoromethylthio;

U is $CH_2$, O, or S; or when one of the dotted lines emanating from U indicates a bond, U is CH; the bond between $Q^1$ or $Q^2$, respectively, and U may also be a triple bond and in such case U is C;

$Q^1$ is elected from a bond, alkylene or alkenylene and $Q^2$ is alkylene having at least two C-atoms, alkenylene or a group $Q^{2'}D$ wherein $Q^{2'}$ is as defined for $Q^2$ and D is $CR^8R^9$ where $R^8$ and $R^9$ are independently selected from the substituents define below for $R^4$–$R^7$, or a cycloalkylene group, $Q^1$ and $Q^2$ having together from 2 to 20 carbon atoms and being optionally substituted with one or more hydroxy groups, any such hydroxy group being optionally esterified with an aliphatic carboxylic acid having from two to twenty four carbon atoms inclusive; and $R^2$ and $R^3$ are independently hydrogen, lower alkyl or they may be linked together by forming an ethylene or propylene bridge;

$R^4$ to $R^7$ are independently selected from hydrogen, halogen, lower alkyl, lower alkoxy, hydroxy, lower alkylthio, lower alkyl- or dialkylamino, cyano, trifluoromethyl, or trifluoromethylthio; and $Z^1$ is a group as defined for $R^4$–$R^7$, $Z^2$ is hydrogen and $Z^3$ is a bond;

or an acid addition salt or a prodrug thereof.

2. The method of claim 1 wherein if X is NH, Y is CH and the dotted line emanating from Y indicates a bond, then —$Q^1$—U—$Q^2$— is not alkyl having less than 5 carbon atoms;

or an acid addition salt or a prodrug thereof.

3. The method of claim 1, wherein Y is CH or $CH_2$; and X is $NR^{10}$ wherein $R^{10}$ is phenyl or substituted phenyl.

4. The method of claim 1, wherein one of $R^4$, $R^5$, $R^6$ or $R^7$ is halogen.

5. The method of claim 1 wherein the halogen is fluorine.

6. The method of claim 1, wherein said piperidine compound is selected from the group consisting of:

3-[4-(4-(2-Methoxyphenyl)-1-piperidinyl)-1-butyl]indole;

2,3-Dihydro-3-[4-(4-(2-methoxyphenyl)-1-piperidinyl)-1-butyl]indol;

3-[6-(4-(4-Fluorophenyl)-1-piperidinyl)-1-hexyl]indole;

3-[4-(4-(3,4-Dichlorophenyl)-1-piperidyl)-1-butyl]indole;

3-[4-(4-(4-Fluorophenyl)-1-piperidyl)-1-butyl]-1,2-benzisoxazole;

5,6-Dichloro-3-[4-(4-(4-fluorophenyl)-1-piperidyl)-1-butyl]-indole;

3-[4-(4-(4-Fluorophenyl)-1-piperidyl)-1-butyl]indol-2-one;

3-[4-(4-Phenyl-1-piperidyl)-1-butyl]indole;

1-Phenyl-3-[4-(4-(4-fluorophenyl)-1-piperidyl)-1-butyl] indole;

2,3-Dihydro-5-fluoro-3-[3-(4-(4-fluorophenyl)-1-piperidinyl)-1-propyl]benzofuran;

3-[3-(4-(4-Fluorophenyl)-piperidin-1-yl)-1-propyloxy]-1,2-benzisothiazole;

3-[4-(4-(2,6-Dichlorophenyl)-1-piperidyl)-1-butyl]-1,2-benzisoxazole; and

3-[4-[3-(4-Fluorophenyl)-8-azabicyclo[3.2.1]octan-8-yl]-1-butyl]-1,2-benzisoxazole;

and pharmaceutically acceptable salts thereof.

7. A method for treating anxiety, psychosis, epilepsy, convulsions, movement disorder, motor disturbance, amnesia, cerebrovascular disease, and senile dementia of Alzheimer's disease, or Parkinson's disease, comprising administering to a patient in need thereof a therapeutically effective amount of a compound having Formula I:

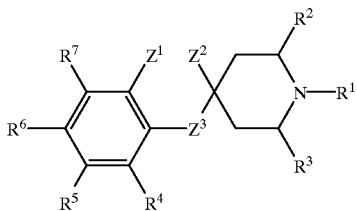

wherein $R^1$ is -D-B-A-R
  wherein B is Ian up to 19 membered spacer group selected from alkylene, alkenylene and alkynylene which is optionally branched or straight chain and optionally substituted with hydroxy, which again is optionally esterified with an aliphatic carboxylic acid having from two to twenty-four carbon atoms, inclusive,
  A is a bond or a divalent group selected from O, S, SO, $SO_2$, and

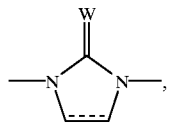

W being O or S and the dashed line designating an optional bond;
  R is alkyl, alkenyl, cycloalkyl, cycloalkenyl, phenyl, cycloalkylalkyl, cycloalkenylalkyl, phenylalkyl, any alkyl group optionally being substituted with one or two hydroxy groups, which again is optionally esterified with an aliphatic carboxylic acid having from two to twenty-four carbon atoms inclusive, and any phenyl group being optionally substituted with one or more substituents on the phenyl ring, and
  D is $CR^8R^9$ where $R^8$ and $R^9$ are independently selected from the substituents defined below for $R^4$–$R^7$, or a cycloalkylene group;
  $R^2$ and $R^3$ are independently hydrogen, lower alkyl or are optionally linked together to form an ethylene or propylene bridge;
  $R^4$ to $R^7$ are independently selected from hydrogen, halogen, lower alkyl, lower alkoxy, hydroxy, lower alkylthio, lower alkylamino and lower dialkylamino; and
  $Z^1$ and $Z^2$ are linked together; wherein $Z^1$ is $CH_2$, O or S; $Z^2$ is $CH_2$, O or S; and $Z^3$ is a bond; with the proviso that $Z^1$ is not S or O when $Z^2$ is S or O; wherein at least one of $Z^1$ and $Z^2$ is O or S; or
  $Z^1$ and $Z^2$ together optionally represent a group —CH=CH—; or $Z^1$ and $Z^2$ together optionally represent a 3-membered divalent group containing one O- or S-heteroatom;
  with the proviso that D-B-A-R is not phenyl-$C_2$, alkyl, cycloalkyl-$C_{2-3}$-alkyl, $C_{3-6}$ lower alkyl or $C_{4-6}$ lower alkenyl, wherein phenyl is optionally substituted with one or more substituents; and if $Z^1$ is O, and $Z^2$ is $CH_2$ then -D-B-A-R is not optionally hydroxy-substitutes hexyl or heptyl;

or an acid addition salt or a prodrug thereof.

8. The method of claim 7 wherein $Z^2$ is O or S and $Z^1$ is $CH_2$.

* * * * *